United States Patent [19]

Urdea et al.

[11] Patent Number: 5,710,264
[45] Date of Patent: Jan. 20, 1998

[54] LARGE COMB TYPE BRANCHED POLYNUCLEOTIDES

[75] Inventors: Michael S. Urdea, Alamo; Thomas Horn, Berkeley; Chu-An Chang, El Cerrito; Brian Warner; Timothy J. Fultz, both of Martinez, all of Calif.

[73] Assignee: Chiron Corporation, Emeryville, Calif.

[21] Appl. No.: 478,085

[22] Filed: Jun. 7, 1995

Related U.S. Application Data

[63] Continuation of Ser. No. 813,588, Dec. 23, 1991, abandoned, which is a continuation-in-part of Ser. No. 558,897, Jul. 27, 1990, abandoned.

[51] Int. Cl.$^6$ .............................. C07H 21/02; C07H 21/04
[52] U.S. Cl. ................................ 536/23.1; 536/24.3
[58] Field of Search .............................. 536/24.3, 23.1, 536/25.3

[56] References Cited

U.S. PATENT DOCUMENTS 5,258,506  11/1993  Urdea et al. ........................ 536/23.1

FOREIGN PATENT DOCUMENTS 0138357  4/1985  European Pat. Off. .
0317077  5/1993  European Pat. Off. .

*Primary Examiner*—Eggerton A. Campbell
*Attorney, Agent, or Firm*—Tyler Dylan; Kenneth M. Goldman; Robert P. Blackburn

[57] ABSTRACT

Large comb-type branched polynucleotides useful as amplifier molecules in nucleic acid hybridization assays are provided, the polynucleotides comprising: a polynucleotide backbone having at least about 15 multifunctional nucleotides, each of which defines a sidechain site and a first single-stranded oligonucleotide unit that is capable of binding specifically to a first single-stranded polynucleotide sequence of interest; and pendant polynucleotide sidechains extending from said multifunctional nucleotides each comprising iterations of a second single-stranded oligonucleotide unit that is capable of binding specifically to a second single-stranded polynucleotide sequence of interest, the total number of iterations in all sidechains being at least 20. Methods of making these polynucleotides are also provided.

36 Claims, No Drawings

LARGE COMB TYPE BRANCHED POLYNUCLEOTIDES

CROSS-REFERENCE TO RELATED APPLICATION

This application is a continuation of U.S. application Ser. No. 08/813,588 filed Dec. 23, 1991, now abandoned, which is a continuation-in-part of U.S. Ser. No. 07/558,897, filed 27, Jul. 1990, now abandoned, hereby incorporated by reference in its entirety.

TECHNICAL FIELD

This invention is in the field of nucleic acid chemistry and biochemical assays. More particularly, it concerns large, comb-type branched polynucleotides that are useful as amplification multimers in nucleic acid hybridization assays.

BACKGROUND

Nucleic acid hybridization assays are commonly used in genetic research, biomedical research and clinical diagnostics. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal that is detected is described in commonly owned European Patent Application (EPA) 883096976 (corresponding to U.S. application Ser. No. 340,031 filed 18, Apr. 1989). It amplifies the signal through the use of amplification multimers. These multimers are polynucleotides that are constructed to have a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are described: fork and comb.

In testing the two types of branched multimers it was found that forked structures of greater than about eight branches exhibited steric hindrance which inhibited binding of labeled probes to the multimer. On the other hand the comb structures exhibited no steric problems and were thus determined to be the preferred type of branched multimer. Unfortunately, however, repeated attempts to make comb structures having more than about 10 branch sites were unsuccessful. Applicants have now developed procedures for producing large comb-type branched multimers. These large comb structures permit a greater degree of amplification than possible previously.

DISCLOSURE OF THE INVENTION

One aspect of the invention is a large comb-type branched polynucleotide comprising:

(a) a polynucleotide backbone having:
  (i) at least about 15 multifunctional nucleotides, each of which defines a sidechain site and
  (ii) a first single-stranded oligonucleotide unit that is capable of binding specifically to a first single-stranded polynucleotide sequence of interest; and
(b) pendant polynucleotide sidechains extending from said multifunctional nucleotides each comprising iterations of a second single-stranded oligonucleotide unit that is capable of binding specifically to a second single-stranded nucleotide sequence of interest.

Another aspect of the invention is a large comb-type branched polynucleotides of the following formula (I) for use as amplification multimers in nucleic acid hybridization assays:

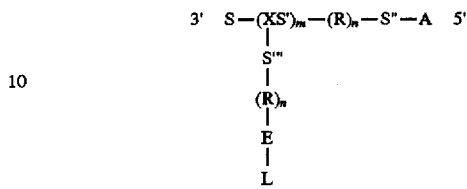

where S is a first spacer segment of at least about 15 nucleotides, X is a modified nucleotide that provides a branch site, S' is a branching site spacer segment of 0 to about 15 nucleotides, m is an integer equal to or greater than 15, R is a cleavable linker molecule, n is 0 or 1, S" is a second spacer segment of about 0 to 10 nucleotides, A is a segment that is capable of hybridizing specifically to analyte nucleic acid or nucleic acid bound to analyte, S'" is a third spacer segment of 0 to 10, E is an oligonucleotide extension of 5 to 10 nucleotides, and L is a segment containing 2 to 10 iterations, of a sequence that is capable of hybridizing specifically to a labeled oligonucleotide probe.

Another aspect of the invention is a large comb-type branched polynucleotide of the formula (II):

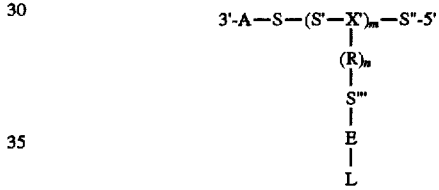

where A is a segment that is capable of hybridizing specifically to analyte nucleic acid or nucleic acid bound to analyte, S is a first spacer segment of at least about 15 molecules, preferably about 15 to 50 molecules, X' is a monomeric molecule that provides a branch site, S' is a branching site spacer segment of 0 to about 15 molecules, preferably 0 to 10 molecules, m is an integer equal to or greater than 15, preferably in the range of 15 to 100, S" is a second spacer segment of about 0 to 10 molecules, preferably 5 to 10 molecules, R is a cleavable linker molecule, n is 0 or 1, S'" is a third spacer segment of 0 to 10 nucleotides, E is an oligonucleotide extension of 5 to 10 nucleotides and L is a segment containing 2 to 10 iterations, preferably 3 to 6 iterations, of a nucleotide sequence that is capable of hybridizing specifically to a labeled oligonucleotide probe.

Another aspect of the invention is a process for making a large comb-type branched polynucleotide comprising:

(a) synthesizing a single-stranded polynucleotide backbone comprising:
  (i) at least about 15 multifunctional nucleotides or monomeric molecules, each of which has a protected functional group that serves as a site for sidechain nucleotide extension and
  (ii) a first ligation site segment;
(b) deprotecting said functional groups;
(c) extending each of said sites at least about five nucleotides to provide second ligation site segments;
(d) ligating a first single-stranded oligonucleotide unit to the first ligation site, said first single-stranded oligonucleotide unit being capable of binding specifically to a first single-stranded nucleic acid sequence of interest; and (e) ligating second single-stranded oligonucleotide units to the second ligation site segments, said second single-stranded oligonucleotide units comprising iterations of a sequence that is capable of binding specifically to a second single-stranded oligonucleotide of interest.

Still another aspect of the invention is an alternative process for making a large comb-type branch polynucleotide useful as an amplification multimer in a nucleic acid hybridization assay comprising:

(a) synthesizing a single-stranded polynucleotide backbone comprising:
   (i) at least about 15 multifunctional nucleotides, each of which has a protected functional group that serves as a site for sidechain nucleotide extension and
   (ii) a first single-stranded oligonucleotide unit that is capable of binding specifically to a first single-stranded polynucleotide sequence of interest;

(b) deprotecting said functional groups;

(c) extending each of said sites at least about five nucleotides to provide ligation site segments; and (d) ligating second single-stranded oligonucleotide units to the ligation site segments said second single-stranded oligonucleotide units comprising iterations of a sequence that is capable of binding to a second single-stranded oligonucleotide of interest.

Yet another aspect of the invention is the use of these large comb-type branched polynucleotides in nucleic acid hybridization assays. In these assays:

(a) the branched polynucleotide is hybridized via the first oligonucleotide unit to single-stranded analyte nucleic acid bound to a solid phase or to a single-stranded oligonucleotide bound to the analyte;

(b) unbound branched polynucleotide is removed;

(c) single-stranded labeled oligonucleotide is hybridized to the branched polynucleotide via the second oligonucleotide units;

(d) unbound labeled oligonucleotide is removed; and (e) the presence of label bound to the branched polynucleotide is detected.

Another aspect of the invention is a branched nucleic acid polymer having a 3' end and two 5' ends provided by the branch, having the structure

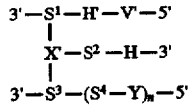

wherein $S^1$ is a first spacer segment of 1 to 100 molecules, preferably 6 to 10 molecules, H' is a first segment comprising a nucleotide sequence of 1 to 100 nucleotides, preferably 6 to 10 nucleotides, V' is a second segment of 1 to 100 nucleotides, preferably 6 to 10 nucleotides, substantially complementary to a sequence of a second oligonucleotide, X' is a monomeric molecule providing a branch site, $S^2$ is a second spacer segment of 1 to 100, molecules, preferably 2 to 8 molecules, H is a third segment comprising a sequence substantially complementary to H', $S^3$ is a third spacer segment of 1 to 100 molecules, preferably 2 to 10 molecules, $S^4$ is a fourth spacer segment of 0 to 100 molecules, preferably 0 to 6 molecules, Y is a third segment of 8 to 100 nucleotides substantially complementary to a third oligonucleotide, and n is 1 to 50, preferably 1 to 5. The spacer segments may comprise nucleotidic or non-nucleotidic molecules. The branched structure facilitates ligation of the 3' end of the polymer to the 5' end of a different single-stranded polynucleotide, which polynucleotide may be the branched comb-type oligonucleotide of the invention.

Another aspect of the invention is a "flex extender" nucleic acid sequence which has a first segment at its 5' or 3' end substantially complementary to a first nucleic acid sequence, 2 to 20 iterations of a second segment which is substantially complementary to a sequence within an amplifier multimer, and may contain a third segment at its 5' or 3' end complementary to a third nucleic acid sequence. The iterations of the second segment are separated by a spacer segment of 6 to 10 molecules, which may be nucleotidic or nonnucleotidic. If nucleotidic, the spacer segment sequences preferably have no homology to other components of the hybridization assay system. The spacer sequences allow increased accessibility to amplifier multimer and confer flexibility to the extender. In one embodiment of the invention, the first segment of the flex extender comprises a unique nucleotide sequence at its 3' end that serves as a ligation sequence allowing ligation to a nucleic acid probe sequence. Ligation is accomplished via a "linker" molecule comprising a segment substantially complementary to the unique sequence at the 3' end of the flex extender molecule and a segment substantially complementary to a unique sequence at the 5' end of the probe molecule.

MODES FOR CARRYING OUT THE INVENTION

A. Definitions

"Large" as used herein to describe the comb-type branched polynucleotides of the invention intends a molecule having at least-about 15 branch sites and at least about 20 iterations of the labeled probe binding sequence.

"Comb-type" as used herein to describe the structure of the branched polynucleotides of the invention intends a polynucleotide having a linear backbone with a multiplicity of sidechains extending from the backbone.

A "multifunctional" or "modified" nucleotide intends a nucleotide monomer which may be stably incorporated into a polynucleotide having an additional functional group, (preferably a cytosine in which the 4-position is modified to provide a functional hydroxy group), to which a nucleotide may be covalently bonded to form a sidechain.

A "branching monomer" intends a monomeric molecule which provides a branch point which may be stably incorporated into a polynucleotide and which has an additional functional group to which a nucleotide may be covalently bonded to form a sidechain. "Branching monomer" includes modified nucleotides and non-nucleotidic molecules.

A "cleavable linker molecule" intends a molecule that may be stably incorporated into a polynucleotide chain and which includes a covalent bond that may be broken or cleaved by chemical treatment or physical treatment such as by irradiation.

An "amplifier multimer or amplification multimer" intends a polynucleotide that is capable of hybridizing directly or indirectly to analyte nucleic acid and to a multiplicity of labeled probes.

B. Characterization of Large Comb-Type Branched Polynucleotides

The polynucleotide multimers of the invention are composed of a linear backbone and pendant sidechains. The backbone includes a segment that provides a specific hybridization site for analyte nucleic acid or nucleic acid bound to the analyte; whereas the pendant sidechains include iterations of a segment that provide specific hybridization sites for a labeled probe.

A first type of preferred embodiments of these comb-type polynucleotide multimers may be represented by the following schematic formula (I):

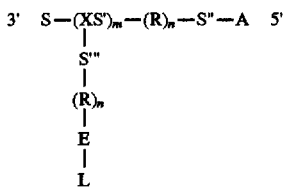

where S is a first spacer segment of at least about 15 nucleotides, preferably about 15 to 50 nucleotides, X is a multifunctional nucleotide that provides a branch site, S' is a branching site spacer segment of 0 to about 15 nucleotides, preferably 0 to 10 nucleotides, m is an integer equal to or greater than 15, preferably in the range of 15 to 100, R is a cleavable linker molecule, n is 0 or 1, S" is a second spacer segment of about 0 to 10 nucleotides, preferably 5 to 10 nucleotides, A is a segment that is capable of hybridizing specifically to analyte nucleic acid or nucleic acid bound to analyte, S'" is a third spacer segment of 0 to 10 nucleotides, E is an oligonucleotide extension of 5 to 10 nucleotides and L is a segment containing 2 to 10 iterations, preferably 3 to 6 iterations, of a nucleotide sequence that is capable of hybridizing specifically to a labeled oligonucleotide probe.

A second type of preferred embodiments of these comb-type polynucleotide multimers may be represented by the following schematic formula (II):

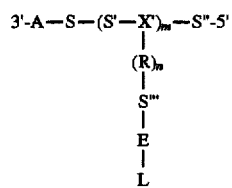

where A is a segment that is capable of hybridizing specifically to analyte nucleic acid or nucleic acid bound to analyte, S is a first spacer segment of at least about 15 molecules, preferably about 15 to 50 molecules, X' is a monomeric molecule that provides a branch site, S' is a branching site spacer segment of 0 to about 15 molecules, preferably 0 to 10 molecules, m is an integer equal to or greater than 15, preferably in the range of 15 to 100, S" is a second spacer segment of about 0 to 10 molecules, preferably 5 to 10 molecules, R is a cleavable linker molecule, n is 0 or 1, S'" is a third spacer segment of 0 to 10 molecules, E is an oligonucleotide extension of 5 to 10 nucleotides and L is a segment containing 2 to 10 iterations, preferably 3 to 6 iterations, of a nucleotide sequence that is capable of hybridizing specifically to a labeled oligonucleotide probe.

The entire backbone of the multimer or the portion thereof from S to S", inclusive, and the portion of the sidechain excluding L will typically be synthesized chemically as an integral unit using conventional automated solid-phase oligonucleotide synthesis chemistry and equipment. In this regard, the spacer segment S serves to space the portion of the molecule that contains the branching sites from the solid phase (the 3' end of S is bound to the surface of the solid phase). In other embodiments of the invention the entire backbone and the pendant sidechains including L may be synthesized as an integral unit.

The modified nucleotides or branching monomers designated X or X' in the above formulae may be a multifunctional nucleotide in which one functional group is used for sidechain extension and the others are used for backbone bonds. Examples of multifunctional nucleotides are described in U.S. Pat. No. 5,124,246 to Undea at al., the disclosure of which is incorporated herein by reference. These modified nucleotides are preferably of the formula:

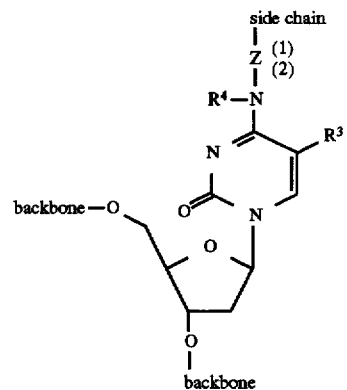

where $R^3$ is hydrogen, methyl I, Br or F, $R^4$ is hydrogen or methyl, Z is selected from the group consisting of

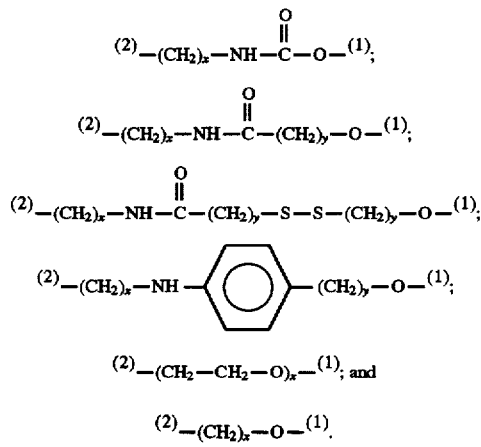

wherein x and y may be the same or different and are integers in the range of 1 to 8, inclusive. (The designations "(1)" and "(2)" at the Z linkage indicate the orientation of the Z linker moiety.)

For multimers of Formula I, as indicated, the spacer segment S' is optional and may be used, if desired, to space each branch site from preceding/succeeding flanking branch sites or a series of adjacent branch sites from flanking series of branch sites. The second spacer segment S" is also optional and may be employed to space the branched portion of the molecule from the segment A to which the analyte is ultimately bound. Such spacing has been found to improve the binding between the analyte and the multimer. Likewise, the third spacer segment S'" is optional. It is preferably polyT.

For multimers of Formula II, as indicated, the spacer segment S' is optional and may be used, if desired, to space each branch site from preceding/succeeding flanking branch sites or a series of adjacent branch sites from flanking series of branch sites. Likewise, the spacer segment S'" is optional. S, S', S", and S'" may comprise nucleotidic or non-nucleotidic molecules. An example of a non-nucleotidic molecule which may be used in a spacer segment is the cleavable linker molecule R, described below.

Segment A has a sequence and length that permits it to bind specifically and stably to the analyte or nucleic acid bound to-the analyte. In order to achieve such specificity and stability segment A will normally be 15 to 50, preferably 15 to 30, nucleotides in length and have a GC content in the range of 40% to 60%. The specific length and sequence of this segment will, of course, vary depending upon the nucleic acid to which it is intended to hybridize.

Segment E is a sidechain extension that is chemically synthesized using automated solid-phase oligonucleotide synthesis equipment and techniques. It is typically about 5 to 10 nucleotides in length and serves as a site to which segment L may be ligated enzymatically.

Segment L comprises iterations of an oligomer unit that is capable of hybridizing specifically and stably to a labeled oligonucleotide probe. These units are also typically 15 to 150, preferably 20 to 120, nucleotides in length and have a GC content in the range of 40% and 60%. Each L segment will normally contain 2 to 10 iterations of the unit, preferably 3 to 6 iterations. Some sidechains may not include an L segment. Normally at least about 50% of the sidechains, preferably at least about 70% of the sidechains, will include an L segment.

The cleavable linker molecules (R) in the backbone and/or sidechains are optional, but preferred. They provide selectable cleavage sites so that samples of the large, comb-type polynucleotide may be cleaved for analysis and characterization purposes. In this regard it is preferred that there be cleavage sites in each sidechain and additional cleavage sites just 5' of the 5' most branch site (for multimers of Formula I) or where the sidechain joins the Examples of cleavable linker molecules that may be incorporated into the polynucleotides are disclosed in EPA 883096976 and in examples, infra.

C. Synthesis of Large Comb-Type Branched Multimers

The polynucleotides of the invention may be assembled using a combination of solid phase direct oligonucleotide synthesis and enzymatic ligation methods.

(I) For multimers of Formula I, the comb body, which includes the 3' spacer (S), branching sites (X), optionally the S' S" and S'" segments, the A segment, optionally the desirable linker molecules (R) and the sidechain extension E, is synthesized by automated solid phase oligonucleotide synthesis techniques. A preferred solid phase is controlled pore glass of at least 2000 Å pore size. In this synthesis spacer segment S is extended from the solid phase. For convenience, this segment is polyT. The multifunctional nucleotides that provide the branch sites are then added to the chain, with or without intervening nucleotides as spacers between branch sites. Orthogonal protecting or blocking groups are used on the modified nucleotides such that the protecting group that permits extension of the backbone may be removed without affecting the protecting group that permits sidechain extension.

Examples of appropriate protecting groups are also described in EPA 883096976. Preferably dimethoxyethyl (DMT) is used as a blocking group on the sugar moiety of the nucleotide. Levulinyl or an anthraquinonyl group of the following formula:

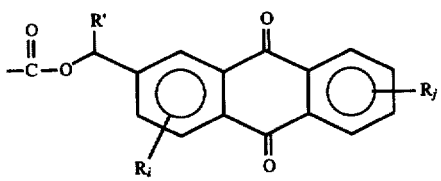

in which R' is hydrogen, aryl, or aralkyl, the $R_i$ may be the same or different and are selected from the group consisting of amino, nitro, halo, hydroxyl, lower alkyl and lower alkoxy; the $R_j$ may be the same or different and are selected from the group consisting of amino, nitro, halo, hydroxyl, lower alkyl and lower alkoxy; i is 0, 1, 2 or 3; and j is 0, 1, 2, 3 or 4, is preferably used as the blocking group on the hydroxyl moiety of the modified nucleotides. After the desired number of branch sites are incorporated, the 5' end of the molecule is extended with the S" (optional) and A segments or simply with a short S" segment (5–10 nucleotides) that provides a site for the enzymatic ligation of the A segment thereto. As indicated above, a selectable cleavage site is preferably incorporated in the extension. If the A segment is synthesized directly rather than being added by ligation, a protecting group, such as 2-methylanthraquinonyl, which may be removed selectively without adversely affecting the rest of the molecule should be used to protect the sidechain sites of the modified nucleotides.

After the 5' end of the comb body has been extended as desired, the groups protecting the hydroxyl moiety of the modified nucleotides are removed and the branching sites are extended simultaneously, preferably with the inclusion of a selectable cleavage site, so that each branch site has at least the 5–10 nucleotide extension (E) that serves as a ligation site.

The L segments (and, if not directly synthesized, the A segment, too) are then ligated to the sidechain extensions by the addition of T4 ligase and appropriate linker templates. The A and L segments and the templates may also be synthesized using available automated solid phase oligonucleotide synthesis equipment and procedures.

(II) For multimers of Formula II, the comb body, which includes the 3' spacer (S), branching site (X'), optionally the S', S", and S'" segments, the A segment, optionally the desirable linker molecules (R) and the sidechain extension E, is synthesized by automated solid phase oligonucleotide synthesis techniques. A preferred solid phase is controlled pore glass of at least 2000 Å pore size. In this synthesis spacer segment S is extended from the solid phase. For convenience, this segment is polyT. The multifunctional nucleotides that provide the branch sites are then added to the chain, with or without intervening nucleotides as spacers between branch sites. Orthogonal protecting or blocking groups are used on the modified nucleotides such that the protecting group that permits extension of the backbone may be removed without affecting the protecting group that permits sidechain extension.

Examples of appropriate protecting groups are also described in EPA 883096976. Preferably dimethoxyethyl (DMT) is used as a blocking group on the sugar moiety of the nucleotide. Levulinyl or an anthraquinonyl group of the following formula:

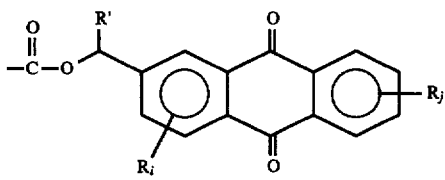

in which R' is hydrogen, aryl, or aralkyl, the $R_i$ may be the same or different and are selected from the group consisting of amino, nitro, halo, hydroxyl, lower alkyl and lower alkoxy; the $R_j$ may be the same or different and are selected from the group consisting of amino, nitro, halo, hydroxyl, lower alkyl and lower alkoxy; i is 0, 1, 2 or 3; and j is 0, 1, 2, 3 or 4, is preferably used as the blocking group on the hydroxyl moiety of the modified nucleotides. After the desired number of branch sites are incorporated, the 5' end of the molecule is extended with the S" (optional). As indicated above, a selectable cleavage site is preferably incorporated in the extension.

After the 5' end of the comb body has been extended as desired, the groups protecting the hydroxyl moiety of the modified nucleotides are removed and the branching sites are then extended, preferably with the inclusion of a selectable cleavage site, so that each branch site has at least the 5–10 nucleotide extension (E) that serves as a ligation site.

The L segments (and, if not directly synthesized, the A segment, too) are then ligated to the sidechain extensions by the addition of T4 ligase and appropriate linker templates. The A and L segments and the templates may also be synthesized using available automated solid phase oligonucleotide synthesis equipment and procedures.

D. Branched Nueleic Acid Polymer with Two 5' Ends

The comb-type multimers described above may be generated by ligation of the E segment of the comb backbone to L via a branched nucleic acid polymer having a 3' end and two 5' ends provided by the branch, having the structure

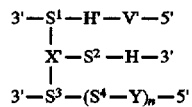

wherein $S^1$ is a first spacer segment of 1 to 100 molecules, preferably 6 to 10 molecules, H' is a first segment comprising a nucleotide sequence of 1 to 100 nucleotides, preferably 6 to 10 nucleotides, V' is a second segment of 1 to 100 nucleotides, preferably 6 to 10 nucleotides, substantially complementary to a sequence of a second oligonucleotide, X' is a monomeric molecule providing a branch site, $S^2$ is a second spacer segment of 1 to 100 molecules, preferably 2 to 8 molecules, H is a segment comprising a sequence substantially complementary to H', $S^3$ is a third spacer segment of 1 to 100 molecules, preferably 2 to 10 molecules, $S^4$ is a fourth spacer segment of 0 to 100 molecules, preferably 0 to 6 molecules, Y is a third segment of 8 to 100 nucleotides substantially complementary to a third oligonucleotide, and n is 1 to 50, preferably 1 to 5. The spacer segments may comprise nucleotidic or non-nucleotidic molecules. The branched structure facilitates ligation of the 3' end of the polymer to the 5' end of a different single-stranded polynucleotide, which polynucleotide may be the branched comb-type oligonucleotide of the invention.

For use with the comb-type multimers of the invention, V' is substantially complementary to the ligation site E in the comb-type multimer described above, and Y is equivalent to L in the comb-type multimer described above, i.e., a segment containing 1 to 50 iterations, preferably 1 to 5 iterations, of a nucleotide sequence that is capable of hybridizing specifically to a labeled oligonucleotide probe as described above. V' and Y may be other sequences capable of specifically hybridizing to other molecules in other assay configurations. Spacer segments $S^1$, $S^2$, $S^3$, and $S^4$ are preferably polyT for convenience.

E. Hybridization Assays

In nucleic acid hybridization assays, a large comb-type multimer of the invention is bound to the analyte nucleic acid or to a single-stranded oligonucleotide bound to the analyte. Since the multimer includes a large number (20 or more) of iterations of a sequence that are available for specific hybridization with the labeled oligonucleotide, many more label groups may be bound to the analyte than in prior procedures. The large number of label groups decreases the threshold level of detectable analyte.

The multimers may be used in essentially any of the known nucleic acid hybridization formats, such as those in which the analyte is bound directly to a solid phase or sandwich hybridizations in which the analyte is bound to an oligonucleotide that is in turn bound to a solid phase. It is particularly useful in the solution phase sandwich hybridization assay formats described in EPA 883096976.

In such solution phase sandwich hybridization assays the multimer is used as follows. Single-stranded analyte nucleic acid is incubated under hybridization conditions with an excess of two single-stranded nucleic acid probe sets: (1) a set of capture probes, each having a first binding sequence substantially complementary to the analyte and a second binding sequence that is substantially complementary to a single-stranded oligonucleotide bound to a solid phase, and (2) a set of amplifier probes, each having a first binding sequence that is capable of specific binding to the analyte and a second binding sequence that is capable of specific binding to the A segment of the multimer. By using an amplifier probe, the multimer may be designed to be a "universal" reagent and different multimers need not be made for each analyte. The resulting product is a three component nucleic acid complex of the two probes hybridized to the analyte by their first binding sequences. The second binding sequences of the probes remain as single-stranded tails as they are not complementary to the analyte.

This complex is then added under hybridizing conditions to a solid phase having a single-stranded oligonucleotide bound to it that is substantially complementary to the second binding sequence of the capture probe. The resulting product comprises the complex bound to the solid phase via the duplex formed by the oligonucleotide bound to the solid phase and the second binding sequence of the capture probe. The solid phase with bound complex is then separated from unbound materials.

The large comb-type amplification multimer is then added to the solid phase-analyte-probe complex under hybridization conditions to permit the multimer to hybridize to the available second binding sequence of the amplifier probe of the complex. The resulting solid phase complex is then separated from any unbound multimer by washing. The labeled oligonucleotide is then added under conditions which permit it to hybridize to the oligonucleotide units on the sidechains of the multimer. The resulting solid phase labeled nucleic acid complex is then separated from excess labeled oligonucleotide, by washing to remove unbound labeled oligonucleotide, and read.

The analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, etc. Also, it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. The analyte sequence is provided in single-stranded form for analysis. Where the sequence is naturally present in single-stranded form, denaturation will not be required. However, where the sequence may be present in double-stranded form, the sequence should be denatured. Denaturation can be carried out by various techniques, such as alkali, generally from about 0.05 to 0.2M hydroxide, formamide, salts, heat, enzymes, or combinations thereof.

The first binding sequences of the capture probe and amplifier probe that are substantially complementary to the analyte sequence will each be of at least 15 nucleotides, usually at least 25 nucleotides, and not more than about 5 kb, usually not more than about 1 kb, preferably not more than about 100 nucleotides. They will typically be approximately 30 nucleotides. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

By appropriate selection of the first binding sequences of the amplifier and capture probes they may be used to identify a specific nucleic acid molecule that includes a particular gene or other sequence that is present as part of different nucleic acid molecules. In order to discriminate the nucleic acid molecule of interest from other molecules that also contain the given sequence, one of the probes is made substantially complementary to the given sequence while the other is made substantially complementary to another sequence of the molecule which other sequence is unique to that molecule (i.e., is not present in the other molecules that contain the given sequence).

The second binding sequences of the capture probe and amplifier probe are selected to be substantially complementary, respectively, to the oligonucleotide attached to the solid phase and to the A segment of the multimer and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probe and amplifier probe may be prepared by oligonucleotide synthesis procedures or by cloning, preferably the former.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary" intends exact complementarity wherein each base within the binding region corresponds exactly, and "substantially complementary" intends 90% or greater homology.

The solid phase that is used in the assay may be particulate or be the solid wall surface of any of a variety of containers, e.g., centrifugal tubes, columns, microtiter plate wells, filters, tubing, etc. When particles are used, they will preferably be of a size in the range of about 0.4 to 200 microns, more usually from about 0.8 to 4.0 microns. The particles may be any convenient material, such as latex, or glass. Microtiter plates are a preferred solid surface. The oligonucleotide that is substantially complementary to the second binding sequence of the capture probe may be stably attached to the solid surface through functional groups by known procedures.

It will be appreciated that one can replace the second binding sequence of the capture probe and the oligonucleotide attached to the solid phase with an appropriate ligand-receptor pair that will form a stable bond joining the solid phase to the first binding sequence of the capture probe. Examples of such pairs are biotin/avidin, thyroxine/thyroxine-binding globulin, antigen/antibody, carbohydrate/lectin, and the like.

The labeled oligonucleotide will include a sequence substantially complementary to the oligonucleotide units on the sidechains of the multimer. The labeled oligonucleotide will include one or more molecules ("labels"), which directly or indirectly provide for a detectable signal. The labels may be bound to individual members of the complementary sequence or may be present as a terminal member or terminal tail having a plurality of labels. Various means for providing labels bound to the sequence have been reported in the literature. See, for example, Leary et al., *Proc Natl Acad Sci USA* (1983) 80:4045; Renz and Kurz, *Nucl Acids Res* (1984) 12:3435; Richardson and Gumport, *Nucl Acids Res* (1983) 11:6167; Smith et al., *Nucl Acids Res* (1985) 13:2399; Meinkoth and Wahl, *Anal Biochem* (1984) 138:267. The labels may be bound either covalently or non-covalently to the complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, $\alpha$-$\beta$-galactosidase, horseradish peroxidase, alkaline phosphatase, etc.

The ratio of capture probe and amplifier probe to anticipated moles of analyte will each be at least stoichiometric and preferably in excess. This ratio is preferably at least about 1.5:1, and more preferably at least 2:1. It will normally be in the range of 2:1 to $10^6$:1. Concentrations of each of the probes will generally range from about $10^{-5}$ to $10^{-9}$M, with sample nucleic acid concentrations varying from $10^{-21}$ to $10^{-12}$M. The hybridization steps of the assay will generally take from about 10 minutes to 20 hours, frequently being completed in about 1 hour. Hybridization can be carried out at a mildly elevated temperature, generally in the range from about 20° C. to 80° C., more usually from about 35° C. to 70° C., particularly 65° C.

The hybridization reaction is usually done in an aqueous medium, particularly a buffered aqueous medium, which may include various additives. Additives which may be employed include low concentrations of detergent (0.1 to 1%), salts, e.g., sodium citrate (0.017 to 0.17M), Ficoll, polyvinylpyrrolidone, carrier nucleic acids, carrier proteins, etc. Nonaqueous solvents may be added to the aqueous medium, such as dimethylformamide, dimethylsulfoxide, alcohols, and formamide. These other solvents are generally present in amounts ranging from 2 to 50%.

The stringency of the hybridization medium may be controlled by temperature, salt concentration, solvent system, and the like. Thus, depending upon the length and nature of the sequence of interest, the stringency will be varied.

The procedure used in the separation steps of the assay will vary depending upon the nature of the solid phase. For particles, centrifugation or filtration will provide for separation of the particles, discarding the supernatant or isolating the supernatant. Where the particles are assayed, the particles will be washed thoroughly, usually from one to five times, with an appropriate buffered medium, e.g., PBS containing a detergent such as SDS. When the separation means is a wall or support, the supernatant may be isolated or discarded and the wall washed in the same manner as indicated for the particles.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

In a hybridization assay in which the analyte nucleic acid is bound directly to a solid phase, such as a "dot blot" assay, the multimer is hybridized directly to the bound analyte. In these instances, the A segment of the multimer is substantially complementary to a sequence of the analyte and the oligonucleotide units on the sidechains are substantially complementary to a labeled oligonucleotide. Unbound multimer is removed from the solid phase and the labeled oligonucleotide is then hybridized to the bound analyte-multimer complex. Excess labeled oligomer is removed and the labeled, bound complex is read.

The multimers may also be used in other assays such as direct, indirect, and sandwich immunoassays. In these instances the reagent that plays the role of the labeled antibody or other ligand that is bound directly or indirectly to the analyte has an oligonucleotide that is substantially complementary to the A segment of the multimer bound to it rather than a label. For instance, in a sandwich immunoassay for an antigen analyte, the analyte sample is incubated with a solid phase to which is bound a first antibody to the antigen. Unbound sample is removed from the solid phase and a second antibody to the antigen and which an oligonucleotide substantially complementary to a unit of the multimer is bound is reacted with the bound complex to form a three-membered complex. Following removal of excess second antibody the multimer is then hybridized to the complex via the oligonucleotide bound to the second antibody. Excess multimer is removed and a labeled oligonucleotide is hybridized to the other oligonucleotide units of the multimer. After removal of excess labeled oligonucleotide, the complex is read.

Kits for carrying out amplified nucleic acid hybridization assays according to the invention will comprise in packaged combination the following reagents: the multimer; an appropriate labeled oligonucleotide; a solid phase that is capable of binding to the analyte; optionally a capture probe if the assay format is one in which the analyte is bound to the solid phase through an intermediate oligonucleotide or other ligand; and optionally an amplifier probe if the assay format is one in which the multimer is not hybridized directly to the analyte. These reagents will typically be in separate containers in the kit. The kit may also include a denaturation reagent for denaturing the analyte, hybridization buffers, wash solutions, enzyme substrates, negative and positive controls and written instructions for carrying out the assay.

The following examples of the invention are offered by way of illustration and not by way of limitation.

EXAMPLES

Example 1

Synthesis of Comb-type Branched Polynulcleotide of Formula I

This example illustrates the synthesis of a comb-type branched polynucleotide of Formula I having 15 branch sites and sidechain extentions having three labeled probe binding sites. This polynucleotide was designed in EPA 883096976.

All chemical synthesis of oligonucletides were performed on an automatic DNA synthesizer (Applied Biosystems, Inc., (ABI) model 380 A/B). Phosphoramidite chemistry of the methoxy type was used except for 5'-phosphorylation which employed Phostel™ reagent (ABN). Standard ABI protoclos were used except as indicated. Where it is indicated that a multiple of a cycle was used (e.g., 1.5×cycle, 4.5×cycle), the multiple of the standard amount of amidite recommended by ABI was employed in the specified cycle. Appended hereto are the programs for carrying out cycles 0.4, 1.5, 4.5, and CAP-PRIM as run on the Applied Biosystems Model 380 A/B DNA Synthesizer.

A comb body of the following structure was first prepared:

where X is a modified mucleotide as described previously.

The portion of the comb body through the 15 repeats is first synthesized using 40 mg thymidine controlled pore glass (CPG) (3000 Å, 3 micromoles thymidine per gram support) with a 1.5×cycle protocol. The branching site nucleotide was of the formula:

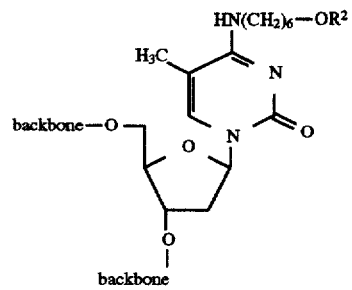

where $R^2$ represents

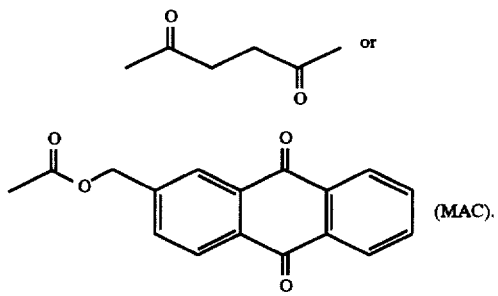

The monomer where $R^2$ represents MAC was made as follows. To a solution of N-4-(6-hydroxyhexyl)-5'-DMT-5-methyl-2'deoxycytidine (17 mmole), prepared as previously described (Horn and Urdea, NAR vol. 17:17, p. 6959–6967 (1989)), in 200 ml methylene chloride was added pyridine (40 mmole) and the mixture cooled to 0° C. A solution of 2-anthraquinonemethoxy chloroformate (MAC-Cl) (20 mmole) in 200 ml of $CH_2Cl_2$ was added dropwise and left stirring for 10 minutes. TLC analysis (silica plates developed with 10% methanol/$CH_2Cl_2$) showed that the starting material had been completely consumed. The reaction mixture was diluted with 400 ml ethyl acetate and the organic phase extracted with 2×300 ml 5% $NaHCO_3$ and 80% saturated aqueous NaCl. After drying of the organic phase over $Na_2SO_4$ for 30 minutes followed by filtration the solvent was removed in vacuo. The product was purified by silica gel chromatography using a gradient of methanol (0–6%) in $CH_2Cl_2$ to give 13 g of pure product (85% yield).

A 0.1 molar solution of 2-(hydroxymethyl)-anthraquinone (MAQ-OH) was prepared by dissolving 25 mmole (5.95 g) in 250 ml dioxane. The yellow solution was filtered and the solvent removed by evaporation to remove water. The residue was redissolved in 200 ml dioxane and pyridine (2 ml; 25 mmole) was added. This solution was added dropwise to a stirred solution of triphosgen (2.5 g; 25 Meq) in 50 ml $CH_2Cl_2$. After ended addition the mixture was stirred at 20° C. for 18 hours. The mixture was diluted with 800 ml ethyl acetate and the organic phase washed with 3×60 ml 80% saturated aqueous NaCl solution. After drying of the organic phase over $Na_2SO_4$ the solvent was removed in vacuo to give a yellow solid, which was dissolved in $CH_2Cl_2$ (250 ml; 0.1M). This solution was used without further purification.

The nucleoside N-4-(O-anthraquinonemethoxy carbonyl-6-oxyhexyl)-5'-DMT-5-methyl-2'-deoxycytidine (14.4 mmole) was dissolved in $CH_2Cl_2$ (50 ml) containing 70 mmole DiPEA. After cooling to 0° C. N,N-diisopropylaminomethoxychlorophosphine was added (2.72 ml; 14 mmole). The phosphitylating agent was added in small portions until 95% of the starting material had been consumed. The reaction mixture was then diluted with ethyl acetate (300 ml), extracted with 2×300 ml 5% $NaHCO_3$ then 2×300 ml 80% saturated aqueous NaCl and finally dried over solid $Na_2SO_4$. The solvent was removed in vacuo.

The crude phosphoramidite was purified by silica gel chromatography. The purified phosphoramidite was dissolved in toluene and added with rapid stirring to 800 ml of cold hexanes (−50° C.). The resulting precipitate was rapidly collected by filtration and dried in high vacuum for 18 hours to give 12.4 g (4.5 mmole, 80% yield) of a slightly yellow solid product. Deprotection of the MAC protected nucleotide is effected by treatment with sodium dithionite under neutral conditions.

For synthesis of the comb body (not including sidechains), the concentration of methylphosphoramidite monomers is 0.1M for A, C, G and T, 0.15M for the branching site monomer X, and 0.2M for Phostel™ reagent. Detritylation was done with 3% trichloroacetic acid in methylene chloride using continuous flow through for the duration of the deprotection. At the conclusion the 5' DMT was replaced with an acetyl group.

Six base sidechain extensions of the formula 3'-GTCAGTp were synthesized at each branching monomer site as follows. The base protecting group removal ($R^2$ in the formula above) was performed manually while retaining the CPG support in the same column used for synthesizing the comb body. In the case of $R^2$=levulinyl, a solution of 0.5M hydrazine hydrate in pyridine/glacial acetic acid (1:1 v/v) is introduced and kept in contact with the CPG support for 90 min with renewal of the liquid every 15 min. After extensive washing with pyridine/glacial acetic acid (4:1 v/v) followed by acetonitrile, the filters in the column are replaced. In the case of $R^2$=2-methylanthraquinonyl a sodium dithionite solution (1 g sodium dithionite dissolved in 20 ml of 1M trimethylammonium bicarbonate, followed by addition of 20 ml of dioxane is introduced and kept in contact with the CPG support for 90 min. After the deprotection the six base sidechain extensions were added using a 4.5×cycle and monomer concentrations of 0.2M.

In these syntheses the concentration of monomers is 0.2M (including R and Phostel™ reagent). Detritylation is effected with a solution of 2.5% dichloroacetic acid in toluene/30% trichloroacetic acid in methylene chloride (1:1 v/v) using continuous flow through. Protecting groups were removed as follows. The phosphate protecting groups were removed from the solid-supported product fragment by treatment of the CPG with a solution of thiophenol/triethylamine/acetonitrile (1:1:2 v/v) for 1 hr at 20° C. followed by washes with acetonitrile (10×1 ml) and methanol. The product fragment was removed from the CPG support by treatment with 0.5 ml concentrated ammonium hydroxide for 20 min and the supernatant was removed. The treatment was repeated twice for a total of one hour exposure. The combined supernatant was transferred to a screw-capped vial and heated at 60° C. for 18 hr. After cooling to room temperature the solvent was removed in a Speed-Vac evaporator and the residue dissolved in 100 μl water.

5' backbone extensions (segment A), sidechain extensions and ligation template/linkers of the following structures were also made using the automatic synthesizer:

| | |
|---|---|
| 5' Backbone extension | 3'-AGGTGCTCCGTATCCTGGGCACAG-5' |
| Sidechain extension | 3'-GATGCGR(TTCATGCTGTTGGTGTAG)$_3$-5' |
| Ligation template for linking 5' backbone extension | 3'-GCACCTACAAAC-5' |
| Ligation template for linking sidechain extension | 3'-CGCATCACTGAC-5' |

R in the sidechain extension represents the following selectable cleavage linker:

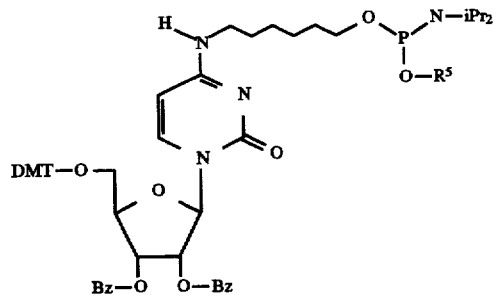

where DMT represents dimethoxyethyl, Bz represents benzoyl, $R^5$ represents methyl or β-cyanoethyl, and iPr represents isopropyl.

Cleavage at the site of R is achieved with a two-step chemical procedure: (1) oxidation with aqueous $NaIO_4$ for 1 hr followed by (2) treatment with aqueous n-propylamine.

The crude comb body was purified by a standard polyacrylamide gel (10% with 7M urea) method.

The 5' backbone extension and the sidechain extensions were ligated to the comb body using a standard T4 ligase protocol (Urdea (1987) Methods in Enzymol. 146:22–41), except that a longer reaction time (>8 hr), 14% polyethylene glycol, and ambient temperature are used.

After ligation and purification, a portion of the product was labeled with $^{32}P$ and subjected to the cleavage steps described above. The sample was then analyzed by PAGE to determine the number of sidechain extensions incorporated by counting the number of bands on the gel. The product was found to have a total of 24 labeled probe binding sites.

Example 2

This example illustrates the preparation of the same multimer as made in Example 1 using a medium pore size CPG/higher loading CPG which is first adjusted to a suitable loading level. Primary synthesis was performed starting from 30 mg thymidine CPG support (1000 Å; 20 mmoles thymidine per gram support). The first 20 coupling cycles with T were performed with the 0.4×cycle to decrease the loading to below ca. 10 mmoles per gram support. This was followed by 20 coupling cycles with T, 15 cycles with X (modified nucleotide), and finally incorporation of the sequence 3'-GTTTGTGGp using the 1.5×cycle. The terminal 5'-DMT group was removed and the sequence capped using the CAP-PRIM cycle program on the ABI machine. The column was removed from the machine and the following manipulations performed manually. Removal of the branch-point levulinate protecting groups was performed as described above, and the resulting CPG support transferred to a new ABI column. Sidechain extension was performed as described above to incorporate the sequence 3'-GTCAGTp using the 4.5×cycle. The protecting groups were removed as described in Example 1 (see above) and the crude product dissolved in 100 μl water.

Ligation of the A and L groups was performed as in Example 1.

Example 3

The 24-site comb-type branched polynucleotide of Example 1 was used in a solution phase sandwich assay for *N. gonorrhoeae* using pilin gene-specific capture and amplifier probes and both $^{32}P$ and alkaline phosphatase-labeled probes as described in Example 5 of EPA 883096976. The two types of labels were used to assess whether use of a 24-site comb structure using alkaline phosphatase labeled probes gave any steric problems. Results were compared to those using a 5-site comb structure which had not exhibited any steric hindrance problems.

When a $^{32}P$ probe was used, the 24 site molecule gave an increase in relative output over the standard 5 site comb of 4.76 (theoretical 4.8; 195,000±10,000 CPM versus 41,000±1,200 CPM, respectively, at 10 attomoles). When an alkaline phosphatase labeled probe was employed, the 24 site molecule gave an increase in relative output over the standard 5 site comb of 3.94 (50.1±1.7 light counts, LC, versus 12.7±0.2 LC, respectively at 10 attomoles). The difference in labeling efficiency with the two types of probes indicates that the enzyme label is accommodated well in the comb structure.

Assays for the other nucleic acid analytes described in the examples of EPA 88309676 may be carried out similarly.

Example 4

Synthesis of Comb-type Branched Polynucleotide of Formula I

This example illustrates the synthesis of a comb-type branched polynucleotide of formula II having 15 branch sites and sidechain extensions having three labeled probe binding sites. This polynucleotide was designed to be used in a solution phase hybridization as described in EPA 883096976.

All chemical syntheses of oligonucleotides were performed on an automatic DNA synthesizer (Applied Biosystems, Inc., (ABI) model 380 B). Phosphoramidite chemistry of the beta cyanoethyl type was used including 5'-phosphorylation which employed Phostel™ reagent (ABN). Standard ABI protocols were used except as indicated. Where it is indicated that a multiple of a cycle was used (e.g., 1.2 cycle), the multiple of the standard amount of amidite recommended by ABI was employed in the specified cycle. Appended hereto are the programs for carrying out cycles 1.2 and 6.4 as run on the Applied Biosystems Model 380 B DNA Synthesizer.

A comb body of the following structure was first prepared:

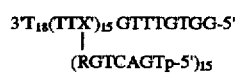

wherein X' is a branching monomer, and R is a periodate cleavable linker.

The portion of the comb body through the 15 (TTX') repeats is first synthesized using 33.8 mg aminopropyl-derivatized thymidine controlled pore glass (CPG) (2000 Å, 7.4 micromoles thymidine per gram support) with a 1.2 cycle protocol. The branching site nucleotide was of the formula:

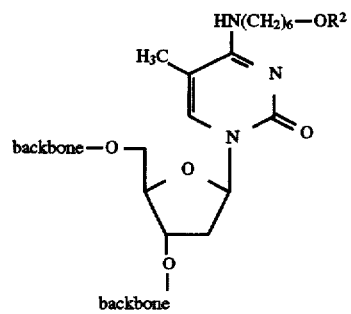

where $R^2$ represents

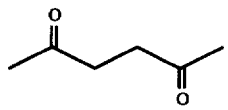

For synthesis of the comb body (not including sidechains), the concentration of beta cyanoethylphosphoramidite monomers was 0.1M for A, C, G and T, 0.15M for the branching site monomer E, and 0.2M for Phostel™ reagent. Detritylation was done with 3% trichloroacetic acid in methylene chloride using stepped flow through for the duration of the deprotection. At the conclusion the 5' DMT was replaced with an acetyl group.

Cleavable linker R and six base sidechain extensions of the formula 3'-RGTCAGTp (SEQ ID NO:1) were synthesized at each branching monomer site as follows. The base protecting group removal ($R^2$ in the formula above) was performed manually while retaining the CPG support in the same column used for synthesizing the comb body. In the case of $R^2$=levulinyl, a solution of 0.5M hydrazine hydrate in pyridine/glacial acetic acid (1:1 v/v) was introduced and kept in contact with the CPG support for 90 min with renewal of the liquid every 15 min, followed by extensive washing with pyridine/glacial acetic acid (1:1 v/v) and then by acetonitrile. After the deprotection the clearable linker R and six base sidechain extensions were added using a 6.4 cycle.

In these syntheses the concentration of phosphoramidites was 0.1M (except 0.2M R and Phostel™ reagent; R was 2-(4-(4-(2-Dimethoxytrityloxy)ethyl-)phenoxy 2,3-di (benzoyloxy)-butyloxy)phenyl)ethyl-2-cyanoethyl-N,N-diisopropylphosphoramidite).

Detritylation is effected with a solution of 3% trichloroacetic acid in methylene chloride using continuous flow through, followed by a rinse solution of toluene/chloromethane (1:1 v/v). Branched polynucleotide chains were removed from the solid supports automatically in the 380B using the cycle "CE NH3." The ammonium hydroxide solution was collected in 4 ml screw-capped Wheaton vials and heated at 60° C. for 12 hr to remove all base-protecting groups. After cooling to room temperature the solvent was removed in a Speed-Vac evaporator and the residue dissolved in 100 µl water.

3' backbone extensions (segment A), sidechain extensions and ligation template/linkers of the following structures were also made using the automatic synthesizer:

This example demonstrates the use of the large comb-type multimer of Example 4 in a hybridization assay for HBV DNA.

A "15×3" amplified solution phase nucleic acid sandwich hybridization assay format was employed in this example. The "15×3" designation derives from the fact that the format employs two multimers: (1) an amplifier probe having a first segment (A) that binds to HBV nucleic acid and a second segment (B) that hybridizes to (2) an amplifier multimer having a first segment (B*) that hybridizes to the segment (B) and fifteen iterations of a segment (C), wherein segment C hybridizes to three labeled oligonucleotides.

The amplifier and capture probe segments and their respective names used in this assay were as follows.

HBV Amplifier Probes

HBV.104* (SEQ ID NO:6)
TTGTGGGTCTTTTGGGYTTTGCTGCYCCWT
HBV.94* (SEQ ID NO:7)
CCTKCTCGTGTTACAGGCGGGGTTTTTCTT
HBV.76* (SEQ ID NO:8)

| | |
|---|---|
| 3' Backbone extension | 3'-TCCGTATCCTGGGCACAGAGGTGCp-5' (SEQ ID NO:2) |
| Sidechain extension | 3'-GATGCG(TTCATGCTGTTGGTGTAG)$_3$-5' (SEQ ID NO:3) |
| Ligation template for linking 3' backbone extension | 3'-AAAAAAAAAAGCACCTp-5' (SEQ ID NO:4) |
| Ligation template for linking sidechain extension | 3'-CGCATCACTGAC-5' (SEQ ID NO:5) |

The crude comb body was purified by a standard polyacrylamide gel (7% with 7M urea and 1X TBE running buffer) method.

The 3' backbone extension and the sidechain extensions were ligated to the comb body as follows. The comb body (4 pmole/µl), 3' backbone extension (6.25 pmole/µl), sidechain extension (93.75 pmole/µl), sidechain linking template (75 pmoles/µl) and backbone linking template (5 pmole/µl) were combined in 1 mM ATP/5 mM DTT/50 mM Tris-HCl, pH 8.0/10 mM MgCl$_2$/2 mM spermidine, with 0.5 units/µl T4 polynucleotide kinase. The mixture was incubated at 37° C. for 2 hr, then heated in a water bath to 95° C., and then slowly cooled to below 35° C. over a 1 hr period. 2 mM ATP, 10 mM DTT, 14% polyethylene glycol, and 0.21 units/µl T4 ligase were added, and the mixture incubated for 16–24 hr at 23° C. The DNA was precipitated in NaCl/ethanol, resuspended in water, and subjected to a second ligation as follows. The mixture was adjusted to 1 mM ATP, 5 mM DTT, 14% polyethylene glycol, 50 mM Tris-HCl, pH 7.5, 10 mM MgCl$_2$, 2 mM spermidine, 0.5 units/µl T4 polynucleotide kinase, and 0.21 units/µl T4 ligase were added, and the mixture incubated at 23° C. for 16–24 hr. Ligation products were then purified by polyacrylamide gel electrophoresis.

After ligation and purification, a portion of the product was labeled with $^{32}$P and subjected to cleavage at the site of R achieved by oxidation with aqueous NaIO$_4$ for 1 hr. The sample was then analyzed by PAGE to determine the number of sidechain extensions incorporated by quantitating the radioactive label in the bands on the gel. The product was found to have a total of 45 labeled probe binding sites.

Example 5

Sandwich Hybridization Assay for HBV DNA using Multimer

TCCATGGCTGCTAGGSTGTRCTGCCAACTG
HBV.87* (SEQ ID NO:9)
GCYTAYAGACCACCAAATGCCCCTATCYTA
HBV.45* (SEQ ID NO:10)
CTGTTCAAGCCTCCAAGCTGTGCCTTGGGT
HBV.93* (SEQ ID NO:11)
CATGGAGARCAYMACATCAGGATTCCTAGG
HBV.99* (SEQ ID NO:12)
TCCTGGYTATCGCTGGATGTGTCTGCGGCGT
HBV.78* (SEQ ID NO:13)
GGCGCTGAATCCYGCGGACGACCCBTCTCG
HBV.81* (SEQ ID NO:14)
CTTCGCTTCACCTCTGCACGTHGCATGGMG
HBV.73* 070590-C (SEQ ID NO:15)
GGTCTSTGCCAAGTGTTTGCTGACGCAACC
HBV.77* 070590-b (SEQ ID NO:16)
CCTKCGCGGGACGTCCTTTGTYTACGTCCC
HBV.D44* 070590-A (SEQ ID NO:17)
MCCTCTGCCTAATCATCTCWTGTWCATGTC
HBV.79* (SEQ ID NO:18)
CGACCACGGGGCGCACCTCTCTTTACGCGG
HBV.82* (SEQ ID NO:19)
TGCCCAAGGTCTTACAYAAGAGGACTCTTG
HBV.71* (SEQ ID NO:20)
CGTCAATCTYCKCGAGGACTGGGGACCCTG
HBV.102* (SEQ ID NO:21)
ATGTTGCCCGTTTGTCCTCTAMTTCCAGGA
HBV. 101* (SEQ ID NO:22)
ATCTTCTTRTTGGTTCTTCTGGAYTAYCAA
HBV.100* (SEQ ID NO:23)
ATCATMTTCCTCTTCATCCTGCTGCTATGC
HBV.98* (SEQ ID NO:24)
CAATCACTCACCAACCTCYTGTCCTCCAAY

HBV.97* (SEQ ID NO:25)
GTGTCYTGGCCAAAATTCGCAGTCCCCAAC
HBV.96* (SEQ ID NO:26)
CTCGTGGTGGACTTCTCTCAATTTTCTAGG
HBV. 95* (SEQ ID NO:27)
GACAAGAATCCTCACAATACCRCAGAGTCT
HBV.92* (SEQ ID NO:28)
TTTTGGGGTGGAGCCCKCAGGCTCAGGGCR
HBV.91*q (SEQ ID NO:29)
CACCATATTCTTGGGAACAAGAKCTACAGC
HBV.88* (SEQ ID NO:30)
ACACTTCCGGARACTACTGTTGTTAGACGA
HBV.86* (SEQ ID NO:31)
GTVTCTTTYGGAGTGTGGATTCGCACTCCT
HBV.D47* (SEQ ID NO:32)
TTGGAGCWWCTGTGGAGTTACTCTCKTTTT
HBV.D46* (SEQ ID NO:33)
TTTGGGGCATGGACATYGAYCCKTATAAAG
HBV.85* (SEQ ID NO:34)
AAWGRTCTTTGTAYTAGGAGGCTGTAGGCA
HBV.84* (SEQ ID NO:35)
RGACTGGGAGGAGYTGGGGGAGGAGATTAG
HBV.83* (SEQ ID NO:36)
CCTTGAGGCMTACTTCAAAGACTGTKTGTT
HBV.80* (SEQ ID NO:37)
GTCTGTGCCTTCTCATCTGCCGGWCCGTGT
HBV.75* (SEQ ID NO:38)
AGCMGCTTGTTTTGCTCGCAGSMGGTCTGG
HBV.74* (SEQ ID NO:39)
GGCTCSTCTGCCGATCCATACTGCGGAACT
HBV.72* (SEQ ID NO:40)
MTKAACCTTTACCCCGTTGCTCGGCAACGG
HBV.51* (SEQ ID NO:41)
GTGGCTCCAGTTCMGGAACAGTAAACCCTG
HBV.67* (SEQ ID NO:42)
KAARCAGGCTTTYAETTTCTCGCCAACTTA
HBV.70* 062890-A (SEQ ID NO:43)
CCTCCKCCTGCCTCYACCAATCGSCAGTCA
HBV.65* (SEQ ID NO:44)
ACCAATTTTCTTYTGTCTYTGGGTATACAT

HBV Capture Probes

HBV.60* (SEQ ID NO:45)
TATTCCCATCCCATCRTCCTGGGCTTTCGS
HBV.64* (SEQ ID NO:46)
TATATGGATGATGTGGTATTGGGGGCCAAG
HBV.63* (SEQ ID NO:47)
CGTAGGGCTTTCCCCCACTGTTTGGCTTTC
HBV.62* (SEQ ID NO:48)
GCTCAGTTTACTAGTGCCATTTGTTCAGTG
HBV.61* (SEQ ID NO:49)
CCTATGGGAGKGGGCCTCAGYCCGTTTCTC
HBV.89* (SEQ ID NO:50)
GTCCCTAGAAGAAGAACTCCCTCGCCTCG
HBV.90* (SEQ ID NO:51)
ACGMAGRTCTCMATCGCCGCGTCGCAGAAGA
HBV.D13* (SEQ ID NO:52)
CAATCTCGGGAATCTCAATGTTAGTATYCC
HBV.D14* (SEQ ID NO:53)
GACTCATAAGGTSGGRAACTTTACKGGGCT

Each amplifier probe contained, in addition to the sequences substantially complementary to the HBV sequences, the following 5' extension complementary to a segment of the amplifier multimer,

AGGCATAGGACCCGTGTCTT (SEQ ID NO:54).

Each capture probe contained, in addition to the sequences substantially complementary to HBV DNA, the following downstream sequence complementary to DNA bound to the solid phase (i.e., complementary to XT1*),

CTTCTTTGGAGAAATTGGTG (SEQ ID NO:55).

Microtiter plates were prepared as follows. White Microlite 1 Removawell strips (polystyrene microtiter plates, 96 wells/plate) were purchased from Dynatech Inc. Each well was filled with 200 μl N HCl and incubated at room temperature for 15–20 min. The plates were then washed 4 times with 1X PBS and the wells aspirated to remove liquid. The wells were then filled with 200 μl N NaOH and incubated at room temperature for 15–20 min. The plates were again washed 4 times with 1X PBS and the wells aspirated to remove liquid.

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/mole. A 1 mg/ml solution of the polypeptide was mixed with 2M NaCl/1X PBS to a final concentration of 0.1 mg/ml (pH 6.0). 100 μL of this solution was added to each well. The plate was wrapped in plastic to prevent drying and incubated at 30° C. overnight. The plate was then washed 4 times with 1X PBS and the wells aspirated to remove liquid.

The following procedure was used to couple the oligonucleotide XT1* to the plates. Synthesis of XT1* was described in EPA 883096976. 20 mg disuccinimidyl suberate was dissolved in 300 μl dimethyl formamide (DMF). 26 $OD_{260}$ units of XT1* was added to 100 μl coupling buffer (50 mM sodium phosphate, pH 7.8). The coupling mixture was then added to the DSS-DMF solution and stirred with a magnetic stirrer for 30 min. An NAP-25 column was equilibrated with 10 mM sodium phosphate, pH 6.5. The coupling mixture DSS-DMF solution was added to 2 ml 10 mM sodium phosphate, pH 6.5, at 4° C. The mixture was vortexed to mix and loaded onto the equilibrated NAP-25 column. DSS-activated XT1* DNA was eluted from the column with 3.5 ml 10 mM sodium phosphate, pH 6.5. 5.6 $OD_{260}$ units of eluted DSS-activated XT1* DNA was added to 1500 ml 50 mM sodium phosphate, pH 7.8. 50 μl of this solution was added to each well and the plates were incubated overnight. The plate was then washed 4 times with 1X PBS and the wells aspirated to remove liquid.

Final stripping of plates was accomplished as follows. 200 L of 0.2N NaOH containing 0.5% (w/v) SDS was added to each well. The plate was wrapped in plastic and incubated at 65° C. for 60 min. The plate was then washed 4 times with 1X PBS and the wells aspirated to remove liquid. The stripped plate was stored with desiccant beads at 2–8° C.

Sample preparation consisted of delivering 12.5 μl P-K buffer (2 mg/ml proteinase K in 10 mM Tris-HCl, pH 8.0/0.15M NaCl/10 mM EDTA, pH 8.0/1% SDS/40 μg/ml sonicated salmon sperm DNA) to each well. A standard curve of HBV DNA was prepared by diluting cloned HBV, subtype adw, DNA in HBV negative human serum and delivering aliquots of dilutions corresponding to 1000, 3000, 10,000, 30,000, or 100,000 molecules to each well. Tests for cross-hybridization to heterologous DNAs were done by adding either purified DNA or infected cells to each well. Amounts for each organism are indicated in the Table.

Plates were covered and agitated to mix samples, then incubated at 65° C. to release nucleic acids.

A cocktail of the HBV-specific amplifier and capture probes listed above was added to each well (5 fmoles of each probe/well, diluted in 1N NaOH). Plates were covered and gently agitated to mix reagents and then incubated at 65° C. for 30 min.

Neutralization-buffer was then added to each well (0.77M 3-(N-morpholino)propane sulfonic acid/1.845M NaCl/0.185 sodium citrate). Plates were covered and incubated for 12-18 hr at 65° C.

After an additional 10 min at room temperature, the contents of each well were aspirated to remove all fluid, and the wells washed 2X with washing buffer (0.1% SDS/ 0.015M NaCl/0.0015 sodium citrate).

Amplifier multimer was then added to each well (30 fmoles/well). After covering plates and agitating to mix the contents in the wells, the plates were incubated for 30 min at 55° C.

After a further 5-10 min period at room temperature, the wells were washed as described above.

Alkaline phosphatase label probe, disclosed in EP 883096976, was then added to each well (40 µl/well of 2.5 fmoles/µl). After incubation at 55° C. for 15 min, and 5 min at room temperature, the wells were washed twice as above and then 3X with 0.015M NaCl/0.0015M sodium citrate.

An enzyme-triggered dioxetane (Schaap et al., Tet. Lett. (1987) 28:1159–1162 and EPA Pub. No. 0254051), obtained from Lumigen, Inc., was employed. 30 µl Lumiphos 530 (Lumigen) was added to each well. The wells were tapped lightly so that the reagent would fall to the bottom and gently swirled to distribute the reagent evenly over the bottom. The wells were covered and incubated at 37° C. for 40 min.

Plates were then read on a Dynatech ML 1000 luminometer. Output was given as the full integral of the light produced during the reaction.

Results from an exclusivity study of the HBV probes is shown in the Table below. Results for each standard sample are expressed as the difference between the mean of the negative control plus two standard deviations and the mean of the sample minus two standard deviations (delta). If delta is greater than zero, the sample is considered positive. These results indicate the ability of these probe sets to distinguish HBV DNA from heterologous organisms and a sensitivity of about 1000-3000 HBV molecules.

TABLE I

| Sample | Amount | Delta |
| --- | --- | --- |
| HBV | $1 \times 10^5$ | 25.99 |
| HBV | $3 \times 10^4$ | 6.51 |
| HBV | $1 \times 10^4$ | 3.00 |
| HBV | $3 \times 10^3$ | 0.93 |
| HBV | $1 \times 10^3$ | -0.20 |
| Contro 1 | — | — |
| HCV | $8 \times 10^5$ | -0.39 |
| CMV[1] | $3.3 \times 10^6$ | -0.48 |
| HTLV-II[2] | $1 \times 10^5$ | -0.07 |
| HTLV-I[2] | $1 \times 10^5$ | -0.23 |
| HIV | $1 \times 10^7$ | -0.31 |
| pBR325 | $1 \times 10^7$ | -0.27 |
| Streptococcus sanguis | $1 \times 10^7$ | -0.31 |
| Streptococcus pyogenes | $1 \times 10^7$ | -0.36 |
| Streptococcus pneuiuoniae | $1 \times 10^7$ | -0.38 |
| Streptococcus fecalis | $1 \times 10^7$ | -0.28 |
| Streptococcus agalactiae | $1 \times 10^7$ | -0.26 |
| Streptococcus epidermidis | $1 \times 10^7$ | -0.31 |
| Staphylococcus aureus | $1 \times 10^7$ | -0.34 |
| Serratia marcescens | $1 \times 10^7$ | -0.30 |
| Pseudomonas aeruginosa | $1 \times 10^7$ | -0.23 |
| Proteus mirabilis | $1 \times 10^7$ | -0.43 |
| Peptostreptococcus anerobius | $1 \times 10^7$ | -0.46 |
| Lactobacillus acidophilus | $1 \times 10^7$ | -0.33 |

TABLE I-continued

| Sample | Amount | Delta |
| --- | --- | --- |
| Klebsiella pneumoniae | $1 \times 10^7$ | -0.12 |
| Haemophilus influenza | $1 \times 10^7$ | -0.34 |
| Escherichia coli | $1 \times 10^7$ | -0.44 |
| Enterobacter aerogenes | $1 \times 10^7$ | -0.23 |
| Mycobacterium leprae | $1 \times 10^7$ | -0.18 |

[1]denotes pfu in infected cells
[2]denotes proviral copies

Example 6

Branched Nucleic Acid Polymer with Two 5' Ends

In this example, the comb-type multimer described above was generated by ligation of the comb backbone to L via a branched nucleic acid polymer having a 3' end and two 5' ends provided by the branch, having the structure

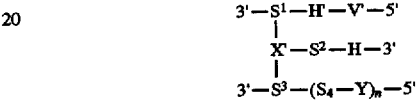

wherein $S^1$ was $T_6$, H' was 5'-CGCATC-3', V' was 5'-ACTGAC-3' (complementary to the ligation site E in the comb body described in Example 4), X' was the modified nucleotide described in Example 4, supra, H was 5'-GCGTAG-3', $S^3$ was $T_2$, $S^4$ was not present (i.e. $S^4$ was zero nucleotides), Y, equivalent to L in Example 4, was 5'-GACGTGGTTGTCGTACTT-3' (SEQ ID NO:56) (BLA3c), and n was 3.

To ligate the branching nucleic acid polymer to the 15×3 comb body, the following mixture was prepared: 15×3 comb body (1500 pmole), a linker of the sequence 5'-TCCACGAAAAAAAAAA-3' (SEQ ID NO:57) (1875 pmole), the 3' backbone extension of Example 4 (2344 pmole), and the branching nucleic acid polymer (35,137 pmole), in 50 mM Tris-HCl, pH 7.5/10 mM MgCl$_2$/2 mM spermidine/1 mM ATP/5 mM dithiothreitol (DTT). After gently mixing, T$_4$ polynucleotide kinase (0.74 units/µl) was added and the reaction mixture (255 µl total volume) incubated for 2 hr at 37° C. The reaction mixture was heated in a water bath to 95° C., then slowly cooled over a 60 min period to 37° C. The mixture was adjusted to 2 mM ATP, 5 mM DTT, 14% polyethylene glycol, T$_4$ ligase (0.21 units/µl) was added, and the mixture (375 µl total volume) incubated at 23° C. for 16-24 hr. NaCl was then added to a final concentration of 0.25M and 2.5 volumes ethanol (95-100%) added to precipitate the nucleic acid.

The DNA was then resuspended in H$_2$O and subjected to a second ligation. The mixture was adjusted to 1 mM ATP, 5 mM DTT, 14% polyethylene glycol, 50 mM Tris-HCl, pH 7.5, 10 mM MgCl$_2$, 2 mM spermidine, and then T4 polynucleotide kinase (0.5 units/µl), and T4 ligase (0.21 units/µl) were added. The reaction mixture (375 µl total volume) was incubated at 23° C. for 16-24 hr, and then precipitated as described above using NaCl/ethanol. The pellet was dissolved in gel loading buffer (90% v/v formamide/1% w/v ficoll/0.05% w/v bromophenol blue) and electrophoresed through a 5% denaturing acrylamide gel. The DNA was visualized using UV shadowing and the band containing the ligated product excised from the gel. The DNA was electroeluted from the gel and precipitated with NaCl/ethanol as described above.

The amplifier multimer made in this fashion was tested in an assay for Hepatitis C virus (HCV) as follows. The assay conditions and probe sequences for HCV were disclosed in commonly owned, copending U.S. Ser. No. 07/697,326, hereby incorporated by reference in its entirety.

A standard curve of HCV RNA was prepared by serially diluting HCV RNA in PK buffer (2 mg/ml proteinase K/40 mM Tris-HCl, pH 8/8 mM EDTA/1% SDS/ 12µg/ml sonicated salmon sperm DNA/4X SSC/5% formamide) to 500, 250, 50, 25, 12.5, or 0 tmoles/150 µl (1 tmole=602 molecules or $10^{-21}$ moles). HCV capture and amplifier probes were added to a final concentration of 0.83 fmoles/µl. The HCV-specific portions of the amplifier probes and capture probes are shown below.

HCV Amplifier Probes

HCV.33.6 (SEQ ID NO:58)
GCATTGAGCGGGTTDATCCAAGAAAGGACCCGG
HCV.33.7 (SEQ ID NO:59)
AGCAGTCTYGCGGGGGCACGCCCAARTCTCCAG
HCV.33.8 (SEQ ID NO:60)
ACAAGGCCTTTCGCGACCCAACACTACTCGGCT
HCV.33.9 (SEQ ID NO:61)
GGGGCACTCGCAAGCACCCTATCAGGCAGTACC
HCV.33.10 (SEQ ID NO:62)
YGTGCTCATGRTGCACGGTCTACGAGACCTCCC
HCV.33.11 (SEQ ID NO:63)
GTTACGTTTGKTTYTTYTTTGRGGTTTRGGAWT
HCV.33.12 (SEQ ID NO:64)
CGGGAACTTRACGTCCTGTGGGCGRCGGTTGGT
HCV.33.13 (SEQ ID NO:65)
CARGTAAACTCCACCRACGATCTGRCCRCCRCC
HCV.33.14 (SEQ ID NO:66)
RCGGCACACCCAAYCTRGGGCCCCT-GCGCGGCAA
HCV.33.15 (SEQ ID NO:67)
AGGTTGCGACCGCTCGGAAGTCTTYCTRGTCGC
HCV.33.16A (SEQ ID NO:68)
RCGHRCCTTGGGGATAGGCTGACGTCWACCTCG
HCV.33.16B (SEQ ID NO:69)
RCGHRCCTTGGGGATAGGTTGTCGCCWTCCACG
HCV.33.17 (SEQ ID NO:70)
YCCRGGCTGRGCCCAGRYCCTRCCCTCGGRYYG
HCV33.18 (SEQ ID NO:71)
BSHRCCCTCRTTRCCRTAGAGGGGCCADGGRTA
HCV.33.19 (SEQ ID NO:72)
GCCRCGGGGWGACAGGAGCCATCCYGCCCACCC
HCV.33.20 (SEQ ID NO:73)
CCCCATGAGRTCGGCGAAGCCGCAYGTRAGGGT
HCV.33.21 (SEQ ID NO:74)
ATCGATGACCTTACCCAARTTRCGCGACCTRCG
HCV.33.22 (SEQ ID NO:75)
CCCCATGAGRTCGGCGAAGCCGCAYGTRAGGGT

HCV Capture Probes

HCV.33.1 (SEQ ID NO:76)
TCCTCACAGGGGAGTGATTCATGGTGGAGTGTC
HCV.33.2 (SEQ ID NO:77)
ATGGCTAGACGCTTTCTGCGTGAAGACAGTAGT
HCV.33.3 (SEQ ID NO:78)
GCCTGGAGGCTGCACGRCACTCATACTAACGCC
HCV.33.4 (SEQ ID NO:79)
CGCAGACCACTATGGCTCTYCCGGGAGGGGGGG
HCV33.5 (SEQ ID NO:80)
TCRTCCYGGCAATTCCGGTGTACTCACCGGTTC
HCV.33.23 (SEQ ID NO:81)
GCCYCCWARRGGGGCGCCGACGAGCGGWATRTA
HCV.33.24 (SEQ ID NO:82)
AACCCGGACRCCRTGYGCCARGGCCCTGGCAGC
HCV.33.25 (SEQ ID NO:83)
RTTCCCTGTTGCATAGTTCACGCCGTCYTCCAG
HCV.33.26 (SEQ ID NO:84)
CARRAGGAAGAKAGAGAAAGAGCAAC-CRGGMAR

Each amplifier probe contained, in addition to the sequences substantially complementary to the HCV sequences, the following 5' extension complementary to a segment of the amplifier multimer,

AGGCATAGGACCCGTGTCTT (SEQ ID NO:54).

Each capture probe contained, in addition to the sequences substantially complementary to HCV DNA, the following downstream sequence complementary to DNA bound to the solid phase (XT1*),

CTTCTTTGGAGAAAGTGGTG (SEQ ID NO:55).

The reaction mixture and 50 µl negative human serum were added to microtiter wells prepared as described above in Example 5. Microtiter plates were incubated overnight at 65° C. The plates were removed from the incubator and were allowed to cool for 10 min at room temperature. The wells were washed 2X with washing buffer (1% SDS/0.015M NaCl/0.0015M sodium citrate). 100 fmoles (in 50 µl) amplifier multimer were added to each well, and then the plates were incubated for 30 min at 55° C. 100 fmoles alkaline phosphatase (AP) label probe described above were added to each well, and the plates were then incubated at 55° C. for 30 min. Plates were cooled at room temperature for 10 min, and then washed 2X with 0.015M NaCl/0.0015 sodium citrate.

An enzyme-triggered dioxetane (Schaap et al., Tet. Lett. (1987) 28:1159–1162 and EPA Pub. No. 0254051), obtained from Lumigen, Inc., was employed. 50 µl Lumiphos 530 (Lumigen) was added to each well. The wells were tapped lightly so that the reagent would fall to the bottom and gently swirled to distribute the reagent evenly over the bottom. The wells were covered and incubated at 37° C. for 40 min.

Plates were then read on a Dynatech ML 1000 luminometer. Output was given as the full integral of the light produced during the reaction.

Results are shown in the Table below. Results for each standard sample are expressed as the difference between the mean of the negative control plus two standard deviations and the mean of the sample minus two standard deviations (delta). If delta is greater than zero, the sample is considered positive. These results indicate a sensitivity of less than 12.5 tmoles of HCV DNA when assayed in this fashion.

TABLE II

| tmoles HCV | delta |
| --- | --- |
| 500 | 27.24 |
| 250 | 8.07 |
| 50 | 0.81 |
| 25 | 1.13 |
| 12.5 | 0.50 |
| 0 | 0 |

Addition of a "flex extender" nucleic acid was performed as described below. The "flex extender" sequence has a 5' segment comprising the sequence 5'-GCGTAG-3', four iterations of a second segment which is substantially complementary to a sequence within an amplifier multimer, and a third segment at the 3' end comprising a sequence substantially complementary to a nucleic acid sequence present in a linker molecule. The iterations of the second segment were separated by a spacer segment of six thymidine residues ($T_6$). The 3' segment of the extender served as a ligation template allowing ligation to an amplifier probe. Ligation was accomplished via a "linker" molecule comprising a segment substantially complementary to the 3' sequence at the end of the extender molecule and a segment substantially complementary to a unique sequence at the 5' end of an amplifier probe. In this example, the 3' segment of the flex extender was 5' TGACTG-3', and the iterated segment was 5'-AGGCATAGGACCCGTGTC-3' (SEQ ID NO:86). The linker molecule had the sequence 5'-ATGCCTCAGTCA-3' (SEQ ID NO:87).

The flex extender was added to the amplifier probe as follows. A mixture of HBV amplifier probes (as described in Example 5 above, 15,625 pmole total), linker (12,500 pmol), and flex extender (10,000 pmol) was made. To this was added 50 mM Tris-HCl, pH 7.5/10 mM $MgCl_2$/2 mM spermidine trihydrochloride/1 mM ATP/50 mM DTT, and 250 units T4 kinase to a final volume of 250 μl. The mixture was incubated at 37° C. for 1–2 hr, and then cooled to room temperature. 90 units T4 ligase were then added, and the mixture incubated at room temperature overnight.

The ligation products were purified as follows. The DNA was precipitated in NaCl/ethanol, and run on a preparative denaturing gel. The DNA band was visualized by UV shadowing and excised. The DNA was electroeluted, resuspended in 10 mM Tris-HCl, pH 8.0/1 mM EDTA, and diluted to 100 fmol/μl.

This extended probe was to be used in an assay for HBV DNA assay as described in Example 5, supra. The amplifier probes of Example 5 were used with the flex extender as described above, and the capture probes used were as described in Example 5.

A cocktail of the HBV-specific amplifier-flex extender and capture probes listed above was added to each well (25 fmoles in 5 μl/well). Plates were covered and gently agitated to mix reagents and then incubated at 65° C. for 30 min.

Neutralization buffer was then added to each well (0.77M 3-(N-morpholino)propane sulfonic acid/1.845M NaCl/0.185 sodium citrate, 3 μl/well). Plates were covered and incubated for 12–18 hr at 65° C.

After an additional 10 min at room temperature, the contents of each well were aspirated to remove all fluid, and the wells washed 2X with 200 μl washing buffer (0.1% SDS/0.015M NaCl/0.0015 sodium citrate).

Amplifier multimer was then added to each well (25 fmoles in 40 μl hybridization buffer/well). After covering plates and agitating to mix the contents in the wells, the plates were incubated for 30 min at 55° C.

After a further 5–10 min period at room temperature, the wells were washed as described above.

Alkaline phosphatase label probe, disclosed in EP 883096976, was then added to each well (40 μl/well of 2.5 fmoles/μl). After incubation at 55° C. for 15 min, and 5 min at room temperature, the wells were washed twice as above and then 3X with 200 μl 0.015M NaCl/0.0015M sodium citrate.

An enzyme-triggered dioxetane (Schaap et al., Tet. Lett. (1987) 28:1159–1162 and EPA Pub. No. 0254051), obtained from Lumigen, Inc., was employed. 30 μl Lumiphos 530 (Lumigen) was added to each well. The wells were tapped lightly so that the reagent would fall to the bottom and gently swirled to distribute the reagent evenly over the bottom. The wells were covered and incubated at 37° C. for 40 min.

Plates were then read on a Dynatech ML 1000 luminometer. Output was given as the full integral of the light produced during the reaction.

Results for each standard sample are expressed as the difference between the mean of the negative control plus two standard deviations and the mean of the sample minus two standard deviations (delta). If delta is greater than zero, the sample is considered positive. These results indicate a sensitivity of between 5 and 10 fmoles DNA.

TABLE III

| fmoles HBV | Delta |
| --- | --- |
| 500 | 155.59 |
| 250 | 87.87 |
| 50 | 19.61 |
| 10 | 5.54 |
| 5 | −0.73 |
| 0 | 0 |

Modifications of the above-described modes for carrying out the invention that are obvious to those of skill in the fields of nucleic acid chemistry and nucleic acid hybridizations are intended to be within the scope of the following claims.

We claim:

1. A large comb-type branched polynucleotide of the formula:

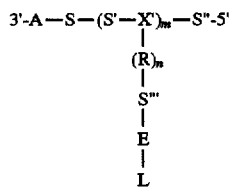

where A is an oligonucleotide substantially complementary to an analyte nucleic acid sequence;

S is a first spacer segment of 1 to 50 linked monomers wherein each of the monomers is independently selected from the group consisting of nucleotides and cleavable linker R;

S' is a branching site spacer segment of 0 to about 15 linked monomers wherein each of the monomers is independently selected from the group consisting of nucleotides and cleavable linker R;

X' is a multifunctional nucleotide that provides a branch site;

m is an integer of 1 to 100;

S" is a second spacer segment of 0 to 10 linked monomers wherein each of the monomers is selected from the group consisting of nucleotides and cleavable linker R;

R is a cleavable linker molecule;

n is 0 or 1;

S'" is a third spacer segment of 0 to 10 linked monomers wherein each of the monomers is selected from the group consisting of nucleotides and cleavable linker R;

E is an oligonucleotide segment of 5 to 10 nucleotides; and

L is an oligonucleotide containing 2 to 10 iterations of a nucleotide sequence substantially complementary to a labeled nucleic acid probe.

2. The branched polynucleotide of claim 1 wherein n is 15.

3. The branched polynucleotide of claim 1 wherein said multifunctional nucleotide has the formula

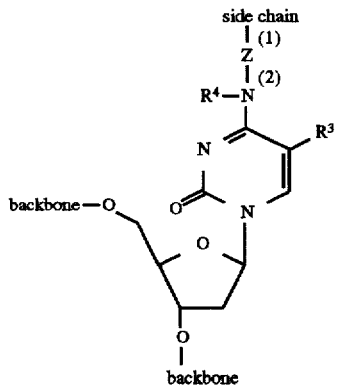

where $R^3$ is hydrogen, methyl, I, Br, or F, $R^4$ is hydrogen or methyl, Z is selected from the group consisting of

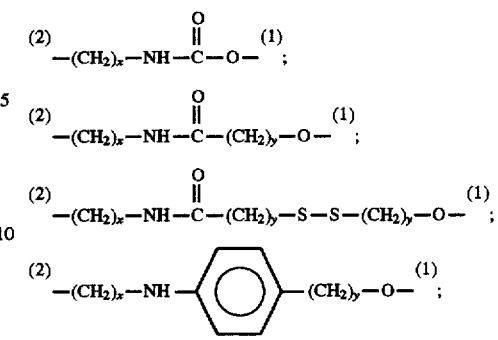

wherein x and y may be the same or different and are integers in the range of 1 to 8 inclusive.

4. The branched polynucleotide of claim 1 wherein S is polyT.

5. The branched polynucleotide of claim 1 wherein n is 1.

6. The branched polynucleotide of claim 1 wherein R is 2-(4-(4-(2-Dimethoxytrityloxy)ethyl-)phenoxy 2,3-di(benzoyloxy)-butyloxy)phenyl)ethyl-2-cyanoethyl-N,N-diisopropylphosphoramidite).

7. A branched nucleic acid polymer having the structure

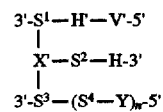

wherein $S^1$ is a first spacer segment of 1 to 100 linked monomers wherein each of the monomers is a independently selected from the group consisting of nucleotides and cleavable linker R;

H' is a segment comprising a nucleotide sequence of 1 to 100 nucleotides;

V' is a second segment of 1 to 100 nucleotides, substantially complementary to a sequence of a second oligonucleotide;

X' is a multifunctional nucleotide that provides a branch site;

$S^2$ is a second spacer segment of 1 to 100 linked monomers wherein each of the monomers is independently selected from the group consisting of nucleotides and cleavable linker R;

H is a segment comprising a nucleotide sequence substantially complementary to H';

$S^3$ is a third spacer segment of 1 to 100 linked monomers wherein each of the monomers is independently selected from the group consisting of nucleotides and clearable linker R;

$S^4$ is a fourth spacer segment of 1 to 100 linked monomers wherein each of the monomers is independently selected from the group consisting of nucleotides and cleavable linker R;

Y is a third segment of 8 to 100 nucleotides comprising a nucleotide sequence substantially complementary to a third oligonucleotide; and n is an integer from 1 to 50.

8. The branched nucleic acid polymer of claim 7, wherein $S^1$, $S^2$, and $S^3$ are polyT.

9. The branched nucleic acid polymer of claim 7, wherein said third oligonucleotide is a labeled oligonucleotide probe.

10. The branched polynucleotide of claim 1, prepared by a process comprising:
   (a) synthesizing a single-stranded polynucleotide backbone comprising:
      (i) at least about 15 branching multifunctional nucleotides, each of which has a protected functional group that serves as an extension site for sidechain nucleotide extension and
      (ii) a segment having a first ligation site;
   (b) deprotecting said functional groups;
   (c) extending each of said extension sites at least about five nucleotides to provide second ligation sites;
   (d) ligating a first single-stranded oligonucleotide unit to the first ligation site, said first single-stranded oligonucleotide unit being capable of binding to a first single-stranded nucleic acid sequence of interest; and
   (e) ligating second single-stranded oligonucleotide units to the second ligation sites, said second single-stranded oligonucleotide units comprising iterations of a sequence that is capable of binding to a second single-stranded nueleic acid sequence of interest.

11. The branched polynucleotide of claim 10, wherein step (e) comprises ligation to the branched nucleic acid polymer having the structure

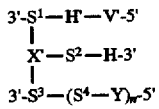

wherein $S^1$ is a first spacer segment of 1 to 100 linked monomers wherein each of the monomers is independently selected from the group consisting of nucleotides and cleavable linker R;

H' is a segment comprising a nucleotide sequence of 1 to 100 nucleotides;

V' is a second segment of 1 to 100 nucleotides, substantially complementary to a sequence of a second oligonucleotide;

X' is a multifunctional nucleotide that provides a branch site;

$S^2$ is a second spacer segment of 1 to 100 linked monomers wherein each of the monomers is independently selected from the group consisting of nucleotides and cleavable linker R;

H is a segment comprising a nucleotide sequence substantially complementary to H';

$S^3$ is a third spacer segment of 1 to 100 linked monomers wherein each of the monomers is independently selected from the group consisting of nucleotides and cleavable linker R;

$S^4$ is a fourth spacer segment of 0 to 100 linked monomers wherein each of the monomers is independently selected from the group consisting of nucleotides and clearable linker R;

Y is a third segment of 8 to 100 nucleotides comprising a nucleotide sequence substantially complementary to a third oligonucleotide;

and n is an integer from 1 to 50.

12. The branched polynucleotide of claim 10 wherein said synthesis and extension are carried out via a solid-phase process in which the 3' end of the backbone is affixed to the solid phase and the backbone includes a 3' leader sequence of at least 18 nucleotides.

13. The branched polynucleotide of claim 12 wherein the solid phase is controlled pore glass of at least 2000 Å pore size.

14. The branched polynucleotide of claim 10 wherein said site for nucleotide extension is extended 5–10 nucleotides.

15. The branched polynucleotide of claim 10 wherein the branching monomeric molecule is of the formula

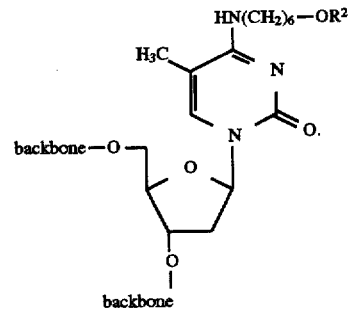

16. A large comb-type branched polynucleotide comprising:
   (a) a polynucleotide backbone having:
      (i) at least about 15 multifunctional nucleotides, each of which defines a sidechain site and
      (ii) a first single-stranded oligonucleotide unit that is capable of binding specifically to a first single-stranded polynucleotide sequence of interest; and
   (b) pendant polynucleotide sidechains extending from said multifunctional nucleotides each comprising iterations of a second single-stranded oligonucleotide unit that is capable of binding specifically to a second single-stranded polynucleotide sequence of interest, the total number of iterations in all sidechains being at least 20.

17. The branched polynucleotide of claim 16 wherein the first single-stranded polynucleotide sequence of interest is analyte nucleic acid or a polynucleotide bound to analyte nucleic acid and the second single-stranded polynucleotide sequence of interest is a labeled polynucleotide.

18. The branched polynucleotide of claim 17 wherein there are 15 to 50 multifunctional nucleotides.

19. The branched polynucleotide of claim 17 wherein the multifunctional nucleotide is of the formula

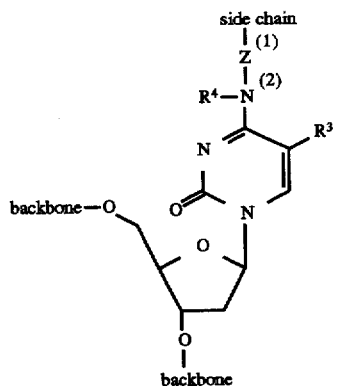

where $R^3$ is hydrogen, methyl, I, Br or F, $R^4$ is hydrogen or methyl, Z is selected from the group consisting of

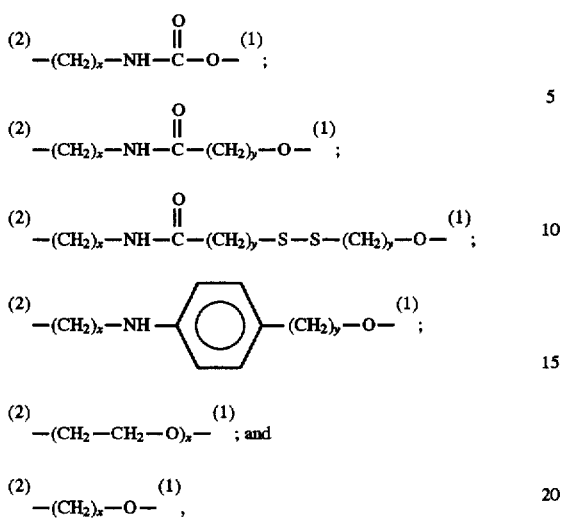

wherein x and y may be the same or different and are integers in the range of 1 to 8 inclusive.

20. The branched polynucleotide of claim 17 wherein the first and second single-stranded oligonucleotide units are each about 15 to 50 nucleotides long.

21. The branched polynucleotide of claim 17 wherein the number of iterations in each sidechain is 2 to 10.

22. The branched polynucleotide of claim 16 wherein the branched polynucleotide is of the formula

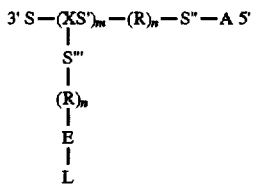

where S is a first spacer segment of at least about 15 nucleotides, X is a multifunctional nucleotide that provides a branch site, S' is a branching site spacer segment of 0 to about 15 nucleotides, m is an integer equal to or greater than 15, R is a cleavable linker molecule, n is 0 or 1, S" is a second spacer segment of about 0 to 10 nucleotides, A is a nucleotide segment that is capable of hybridizing specifically to analyte nucleic acid or nucleic acid bound to analyte, S'" is a third spacer segment of 0 to 10 nucleotides, E is an oligonucleotide extension of 5 to 10 nucleotides, and L is a segment containing 2 to 10 iterations, of a nucleotide sequence that is capable of hybridizing specifically to a labeled oligonucleotide probe.

23. The branched polynucleotide of claim 22 wherein S is 15 to 50 nucleotides in length, X is of the formula

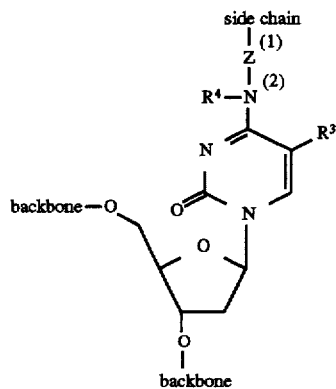

where $R^3$ is hydrogen, methyl, I, Br or F, $R^4$ is hydrogen or methyl, Z is selected from the group consisting of

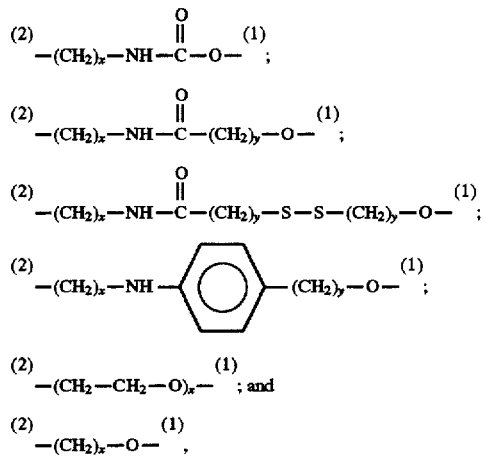

wherein x and y may be the same or different and are integers in the range of 1 to 8 inclusive, S" is 5 to 10 nucleotides in length, and the number of iterations in L is 3 to 6.

24. The branched polynucleotide of claim 23 wherein S is polyT.

25. The branched polynucleotide of claim 23 wherein n is 1.

26. The branched polynucleotide of claim 25 wherein the cleavable linker molecule is of the formula

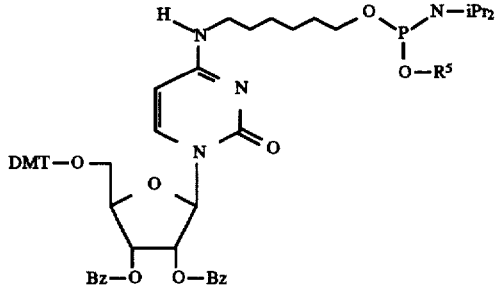

where DMT represents dimethoxyethyl, Bz represents benzoyl, $R^5$ represents methyl or β-cyanoethyl, and iPr represents isopropyl.

27. The branched polynucleotide of claim 16 or claim 22 prepared by a process comprising:

(a) synthesizing a single-stranded polynucleotide backbone comprising:

(i) at least about 15 multifunctional nucleotides, each of which has a protected functional group that serves as an extension site for sidechain nucleotide extension and (ii) a segment having a first ligation site;

(b) deprotecting said functional groups;

(c) extending each of said extension sites at least about five nucleotides to provide second ligation sites;

(d) ligating a first single-stranded oligonucleotide unit to the first ligation site, said first single-stranded oligonucleotide unit being capable of binding to a first single-stranded nucleic acid sequence of interest; and (e) ligating second single-stranded oligonucleotide units to the second ligation sites, said second single-stranded oligonucleotide units comprising iterations of a sequence that is capable of binding to a second single-stranded nucleic acid sequence of interest.

28. The branched polynucleotide of claim 27 wherein said synthesis and extension are carried out via a solid-phase process in which the 3' end of the backbone is affixed to the solid phase and the backbone includes a 3' leader sequence of at least about 15 nucleotides.

29. The branched polynucleotide of claim 28 wherein the solid phase is controlled pore glass of at least 2000 Å pore size.

30. The branched polynucleotide of claim 29 wherein said site for nucleotide extension is extended 5–10 nucleotides.

31. The branched polynucleotide of claim 28 wherein the multifunctional nucleotide is of the formula

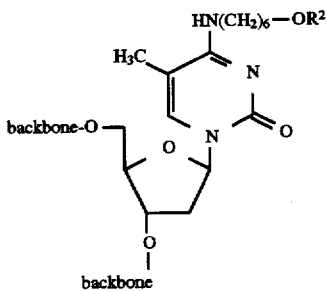

where R² represents

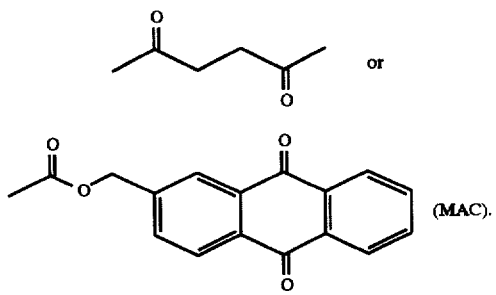

32. The branch polynucleotide of claim 16 or claim 22 useful as an amplification multimer in a nucleic acid hybridization assay prepared by a process comprising:

(a) synthesizing a single-stranded polynucleotide backbone comprising:

(i) at least about 15 multifunctional nucleotides, each of which has a protected functional group that serves as a site for sidechain nucleotide extension and (ii) a first single-stranded oligonucleotide unit that is capable of binding specifically to a first single-stranded polynucleotide sequence of interest;

(b) deprotecting said functional groups;

(c) extending each of said sites at least about five nucleotides to provide ligation site segments; and (d) ligating second single-stranded oligonucleotide traits to the ligation site segments said second single-stranded oligonucleotide units comprising iterations of a sequence that is capable of binding to a second single-stranded oligonucleotide of interest.

33. The branched polynucleotide of claim 32 wherein the multifunctional nucleotide is of the formula

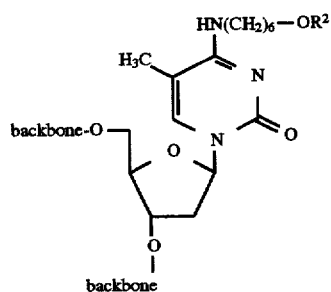

where R² represents

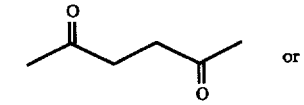

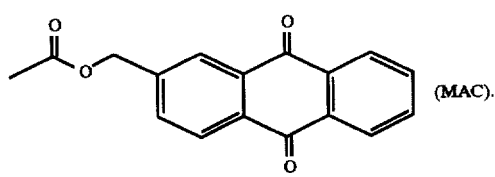

34. The branched polynucleotide of claim 33 wherein said synthesis and extension are carried out via a solid-phase process in which the 3' end of the backbone is affixed to the solid phase and the backbone includes a 3' spacer sequence of at least about 15 nucleotides.

35. The branched polynucleotide of claim 33 wherein the solid phase is controlled pore glass of at least 2000 Å pore size.

36. The branched polynucleotide of claim 33 wherein said site for nucleotide extension is extended 5–10 nucleotides.

* * * * *

SEQUENCE LISTING ( 1 ) GENERAL INFORMATION:

( i i i ) NUMBER OF SEQUENCES: 87

( 2 ) INFORMATION FOR SEQ ID NO:1:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TGACTGR        7

( 2 ) INFORMATION FOR SEQ ID NO:2:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

CGTGGAGACA CGGGTCCTAT GCCT    24

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GATGTGGTTG TCGTACTTGA TGTGGTTGTC GTACTTGATG TGGTTGTCGT ACTTGCGTAG    60

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCCACGAAAA AAAAAA    16

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CAGTCACTAC GC    12

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TTGTGGGTCT TTTGGGYTTT GCTGCYCCWT    30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CCTKCTCGTG TTACAGGCGG GGTTTTTCTT    30

( 2 ) INFORMATION FOR SEQ ID NO:8:

( i ) SEQUENCE CHARACTERISTICS:

(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:8:

TCCATGGCTG CTAGGSTGTR CTGCCAACTG  30

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:9:

GCYTAYAGAC CACCAAATGC CCCTATCYTA  30

(2) INFORMATION FOR SEQ ID NO:10:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:10:

CTGTTCAAGC CTCCAAGCTG TGCCTTGGGT  30

(2) INFORMATION FOR SEQ ID NO:11:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:11:

CATGGAGARC AYMACATCAG GATTCCTAGG  30

(2) INFORMATION FOR SEQ ID NO:12:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:12:

TCCTGGYTAT CGCTGGATGT GTCTGCGGCG T  31

(2) INFORMATION FOR SEQ ID NO:13:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:13:

GGCGCTGAAT CCYGCGGACG ACCCBTCTCG  30

(2) INFORMATION FOR SEQ ID NO:14:

(i) SEQUENCE CHARACTERISTICS:
(A) LENGTH: 30 base pairs
(B) TYPE: nucleic acid ( C ) STRANDEDNESS: single
( D ) TOPOLOGY: linear ( x i ) SEQUENCE DESCRIPTION: SEQ ID NO:14:

CTTCGCTTCA CCTCTGCACG THGCATGGMG   30

( 2 ) INFORMATION FOR SEQ ID NO:15:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:15:

GGTCTSTGCC AAGTGTTTGC TGACGCAACC   30

( 2 ) INFORMATION FOR SEQ ID NO:16:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:16:

CCTKCGCGGG ACGTCCTTTG TYTACGTCCC   30

( 2 ) INFORMATION FOR SEQ ID NO:17:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:17:

MCCTCTGCCT AATCATCTCW TGTWCATGTC   30

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:18:

CGACCACGGG GCGCACCTCT CTTTACGCGG   30

( 2 ) INFORMATION FOR SEQ ID NO:19:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:19:

TGCCCAAGGT CTTACAYAAG AGGACTCTTG   30

( 2 ) INFORMATION FOR SEQ ID NO:20:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:20:

CGTCAATCTY CKCGAGGACT GGGGACCCTG                    30

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

ATGTTGCCCG TTTGTCCTCT AMTTCCAGGA                    30

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

ATCTTCTTRT TGGTTCTTCT GGAYTAYCAA                    30

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

ATCATMTTCC TCTTCATCCT GCTGCTATGC                    30

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CAATCACTCA CCAACCTCYT GTCCTCCAAY                    30

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GTGTCYTGGC CAAAATTCGC AGTCCCCAAC                    30

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CTCGTGGTGG ACTTCTCTCA ATTTTCTAGG 30

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GACAAGAATC CTCACAATAC CRCAGAGTCT 30

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

TTTTGGGGTG GAGCCCKCAG GCTCAGGGCR 30

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

CACCATATTC TTGGGAACAA GAKCTACAGC 30

( 2 ) INFORMATION FOR SEQ ID NO:30:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

ACACTTCCGG ARACTACTGT TGTTAGACGA 30

( 2 ) INFORMATION FOR SEQ ID NO:31:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

GTVTCTTTYG GAGTGTGGAT TCGCACTCCT 30

( 2 ) INFORMATION FOR SEQ ID NO:32:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

TTGGAGCWWC TGTGGAGTTA CTCTCKTTTT 30

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

TTTGGGGCAT GGACAT Y GAY CCKTATAAAG       30

( 2 ) INFORMATION FOR SEQ ID NO:34:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

AAWGRTCTTT GTAYTAGGAG GCTGTAGGCA       30

( 2 ) INFORMATION FOR SEQ ID NO:35:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

RGACTGGGAG GAGYTGGGGG AGGAGATTAG       30

( 2 ) INFORMATION FOR SEQ ID NO:36:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

CCTTGAGGCM TACTTCAAAG ACTGTKTGTT       30

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GTCTGTGCCT TCTCATCTGC CGGWCCGTGT       30

( 2 ) INFORMATION FOR SEQ ID NO:38:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

AGCMGCTTGT TTTGCTCGCA GSMGGTCTGG       30

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GGCTCSTCTG CCGATCCATA CTGCGGAACT          30

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

MTKAACCTTT ACCCCGTTGC TCGGCAACGG          30

( 2 ) INFORMATION FOR SEQ ID NO:41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GTGGCTCCAG TTCMGGAACA GTAAACCCTG          30

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

KAARCAGGCT TTYACTTTCT CGCCAACTTA          30

( 2 ) INFORMATION FOR SEQ ID NO:43:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

CCTCCKCCTG CCTCYACCAA TCGSCAGTCA          30

( 2 ) INFORMATION FOR SEQ ID NO:44:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

ACCAATTTTC TTYTGTCTYT GGGTATACAT          30

( 2 ) INFORMATION FOR SEQ ID NO:45:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:45:

TATTCCCATC CCATCRTCCT GGGCTTTCGS   30

( 2 ) INFORMATION FOR SEQ ID NO:46:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:46:

TATATGGATG ATGTGGTATT GGGGGCCAAG   30

( 2 ) INFORMATION FOR SEQ ID NO:47:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:47:

CGTAGGGCTT TCCCCCACTG TTTGGCTTTC   30

( 2 ) INFORMATION FOR SEQ ID NO:48:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:48:

GCTCAGTTTA CTAGTGCCAT TTGTTCAGTG   30

( 2 ) INFORMATION FOR SEQ ID NO:49:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:49:

CCTATGGGAG KGGGCCTCAG YCCGTTTCTC   30

( 2 ) INFORMATION FOR SEQ ID NO:50:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:50:

GTCCCCTAGA AGAAGAACTC CCTCGCCTCG   30

( 2 ) INFORMATION FOR SEQ ID NO:51:

( i ) SEQUENCE CHARACTERISTICS:
  ( A ) LENGTH: 31 base pairs ( B ) TYPE: nucleic acid
        ( C ) STRANDEDNESS: single
        ( D ) TOPOLOGY: linear ( x i ) SEQUENCE DESCRIPTION: SEQ ID NO:51:

ACGMAGRTCT CMATCGCCGC GTCGCAGAAG A    31

( 2 ) INFORMATION FOR SEQ ID NO:52:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

CAATCTCGGG AATCTCAATG TTAGTATYCC    30

( 2 ) INFORMATION FOR SEQ ID NO:53:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

GACTCATAAG GTSGGRAACT TTACKGGGCT    30

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

AGGCATAGGA CCCGTGTCTT    20

( 2 ) INFORMATION FOR SEQ ID NO:55:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

CTTCTTTGGA GAAAGTGGTG    20

( 2 ) INFORMATION FOR SEQ ID NO:56:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GACGTGGTTG TCGTACTT    18

( 2 ) INFORMATION FOR SEQ ID NO:57:

( i ) SEQUENCE CHARACTERISTICS:
        ( A ) LENGTH: 16 base pairs
        ( B ) TYPE: nucleic acid
        ( C ) STRANDEDNESS: single ( D ) TOPOLOGY: linear ( x i ) SEQUENCE DESCRIPTION: SEQ ID NO:57:

TCCACGAAAA AAAAAA                                                                                          16

( 2 ) INFORMATION FOR SEQ ID NO:58:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:58:

GCATTGAGCG GGTTDATCCA AGAAAGGACC CGG                                                                        33

( 2 ) INFORMATION FOR SEQ ID NO:59:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:59:

AGCAGTCTYG CGGGGGCACG CCCAARTCTC CAG                                                                        33

( 2 ) INFORMATION FOR SEQ ID NO:60:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:60:

ACAAGGCCTT TCGCGACCCA ACACTACTCG GCT                                                                        33

( 2 ) INFORMATION FOR SEQ ID NO:61:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:61:

GGGGCACTCG CAAGCACCCT ATCAGGCAGT ACC                                                                        33

( 2 ) INFORMATION FOR SEQ ID NO:62:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:62:

YGTGCTCATG RTGCACGGTC TACGAGACCT CCC                                                                        33

( 2 ) INFORMATION FOR SEQ ID NO:63:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear (x i) SEQUENCE DESCRIPTION: SEQ ID NO:63:

GTTACGTTTG KTTYTTYTTT GRGGTTTRGG AWT                    33

(2) INFORMATION FOR SEQ ID NO:64:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (x i) SEQUENCE DESCRIPTION: SEQ ID NO:64:

CGGGAACTTR ACGTCCTGTG GGCGRCGGTT GGT                    33

(2) INFORMATION FOR SEQ ID NO:65:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (x i) SEQUENCE DESCRIPTION: SEQ ID NO:65:

CARGTAAACT CCACCRACGA TCTGRCCRCC RCC                    33

(2) INFORMATION FOR SEQ ID NO:66:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (x i) SEQUENCE DESCRIPTION: SEQ ID NO:66:

RCGGCACACC CAAYCTRGGG CCCCTGCGCG GCAA                   34

(2) INFORMATION FOR SEQ ID NO:67:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (x i) SEQUENCE DESCRIPTION: SEQ ID NO:67:

AGGTTGCGAC CGCTCGGAAG TCTTYCTRGT CGC                    33

(2) INFORMATION FOR SEQ ID NO:68:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (x i) SEQUENCE DESCRIPTION: SEQ ID NO:68:

RCGHRCCTTG GGGATAGGCT GACGTCWACC TCG                    33

(2) INFORMATION FOR SEQ ID NO:69:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (x i) SEQUENCE DESCRIPTION: SEQ ID NO:69:

RCGHRCCTTG GGGATAGGTT GTCGCCWTCC ACG              33

( 2 ) INFORMATION FOR SEQ ID NO:70:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

YCCRGGCTGR GCCCAGRYCC TRCCCTCGGR YYG              33

( 2 ) INFORMATION FOR SEQ ID NO:71:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

BSHRCCCTCR TTRCCRTAGA GGGGCCADGG RTA              33

( 2 ) INFORMATION FOR SEQ ID NO:72:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

GCCRCGGGGW GACAGGAGCC ATCCYGCCCA CCC              33

( 2 ) INFORMATION FOR SEQ ID NO:73:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

CCCCATGAGR TCGGCGAAGC CGCAYGTRAG GGT              33

( 2 ) INFORMATION FOR SEQ ID NO:74:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

ATCGATGACC TTACCCAART TRCGCGACCT RCG              33

( 2 ) INFORMATION FOR SEQ ID NO:75:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

CCCCATGAGR TCGGCGAAGC CGCAYGTRAG GGT              33

(2) INFORMATION FOR SEQ ID NO:76:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:76:

TCCTCACAGG GGAGTGATTC ATGGTGGAGT GTC        33

(2) INFORMATION FOR SEQ ID NO:77:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:77:

ATGGCTAGAC GCTTTCTGCG TGAAGACAGT AGT        33

(2) INFORMATION FOR SEQ ID NO:78:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:78:

GCCTGGAGGC TGCACGRCAC TCATACTAAC GCC        33

(2) INFORMATION FOR SEQ ID NO:79:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:79:

CGCAGACCAC TATGGCTCTY CCGGGAGGGG GGG        33

(2) INFORMATION FOR SEQ ID NO:80:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:80:

TCRTCCYGGC AATTCCGGTG TACTCACCGG TTC        33

(2) INFORMATION FOR SEQ ID NO:81:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:81:

GCC Y CCWARR GGGGCGCCGA CGAGCGGWAT RTA        33

(2) INFORMATION FOR SEQ ID NO:82:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:82:

AACCCGGACR CCRTGYGCCA RGGCCCTGGC AGC       33

( 2 ) INFORMATION FOR SEQ ID NO:83:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

RTTCCCTGTT GCATAGTTCA CGCCGTCYTC CAG       33

( 2 ) INFORMATION FOR SEQ ID NO:84:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

CARRAGGAAG AKAGAGAAAG AGCAACCRGG MAR       33

( 2 ) INFORMATION FOR SEQ ID NO:85:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

GCGTAGGATG TGGTTGTCGT AGTACTTGAT GTGGTTGTCG TAGTACTTGA TGTGGTTGTC       60

GTAGTACTT       69

( 2 ) INFORMATION FOR SEQ ID NO:86:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

AGGCATAGGA CCCGTGTC       18

( 2 ) INFORMATION FOR SEQ ID NO:87:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

ATGCCTCAGT CA       12